US005998154A

United States Patent [19]

Schonbrunn

[11] Patent Number: 5,998,154

[45] **Date of Patent: *Dec. 7, 1999**

[54] SOMATOSTATIN RECEPTOR PEPTIDE ANTIGENS AND ANTIBODIES

[75] Inventor: Agnes Schonbrunn, Houston, Tex.

[73] Assignee: The University of Texas System, Austin, Tex.

[ * ] Notice: This patent issued on a continued prosecution application filed under 37 CFR 1.53(d), and is subject to the twenty year patent term provisions of 35 U.S.C. 154(a)(2).

[21] Appl. No.: 08/499,676

[22] Filed: Jul. 7, 1995

[51] Int. Cl.[6] .......................... G01N 35/53; C07K 16/28; C07K 14/705; C07K 14/47

[52] U.S. Cl. .......................... 435/7.21; 435/7.1; 435/7.2; 435/7.23; 435/7.5; 435/7.9; 435/7.91; 435/7.92; 436/63; 436/64; 436/547; 424/184.1; 424/185.1; 424/192.1; 424/193.1; 424/278.1; 530/300; 530/325; 530/326; 530/350; 530/387.1; 530/387.9; 530/403; 530/413

[58] Field of Search ............................ 435/7.1, 7.2, 7.21, 435/7.91, 7.92, 7.23, 7.5, 7.9; 530/300, 326, 327, 387.9, 391.3, 389.1, 324, 325, 350, 387.1, 403, 413; 436/63, 64, 547; 424/184.1, 185.1, 192.1, 193.1, 278

[56] References Cited

U.S. PATENT DOCUMENTS 5,331,094 7/1994 Eppler et al. .

FOREIGN PATENT DOCUMENTS

0508221A1 10/1992 European Pat. Off. .
WO 93/131130 7/1993 WIPO .

OTHER PUBLICATIONS

Bell, Graeme I. et al. (1995) "Molecular Biology of Somatostatin Receptors" in 1995 Somatostatin and its receptors. Wiley, Chichester Ciba Foundation Symposium, p. 65–88.

Berelowitz, Michael et al. (1995) "Regulation of Somatostatin Receptor mRNA Expression" in 1995 Somatostatin and its receptors. Wiley, Chichester Ciba Foundation Symposium, p. 111–126.

Birnbaumer, Lutz et al. (1990) "Receptor–effector Coupling by G Proteins" Biochimica et Biophysica Acta, 1031:163–224.

Brown, Patricia J. et al. (1990) Identification of Somatostatin Receptors by Covalent Labeling with a Novel Photoreactive Somatostatin Analog' The Journal of Biological Chemistry 265(29):17995–18004.

Brown, Patricia J. and Schonbrunn, Agnes (1993) "Affinity Purification of a Somatostatin Receptor–G–protein Complex Demonstrates Specificity in Receptor–G–protein Coupling" The Journal of Biological Chemistry 268(9):6668–6676.

Brown, P. J. et al. (1993) "Selective Immunoprecipitation of Somatostatin Receptor Subtype 1 (SSR1) with an Antipeptide Antibody" In The Proceedings of the 75th Meetings of the Endocrine Society, p. 410.

Bruno, John F. (1992) "Molecular Cloning and Functional Expression of a Brain–Specific Somatostatin Receptor" Proc. Natl. Acad. Sci. USA 89:11151–11155.

Bruns, Christian et al. (1994) "Molecular Pharmacology of Somatostatin–receptor Subtypes" Annals of the NY Acad. Sci 733:138–146.

Bruns, Ch. et al. (1995) "Characterization of Somatostatin Receptor Subtypes" in 1995 Somatostatin and its receptors. Wiley, Chichester Ciba Foundation Symposium, p. 89–110.

Carlson, G. L., et al. (1994) "Somatostatin in Gastroenterology" BMJ 309:604–605.

Coy, David H. et al. (1995) "Somatostatin Analogues and Multiple Receptors: Possible Physiological Roles" in 1995 Somatostatin and its receptors. Wiley, Chichester Ciba Foundation Symposium, p. 240–254.

Estes, Heather G. (1992) "At Least Three Distinct Proteins are Necessary for the Reconstitution of a Specific Multiprotein Complex at a Eukaryotic Chromosomal Origin of Replication" Proc. Natl. Acad. Sci. USA 89:11156–11160.

Ezzat, Shereen and Shlomo Melmed (1992) "Endocrine Applications of the Somatostatin Analogue Octreotide (Sandostatin®)" Metabolism 41(9)suppl 2:34–38.

Gu, Yi–Zhong et al. (1995) "Distribution and G Protein Coupling of Somatostatin Receptor 2A (SSTR2A) Characterized by a Receptor Specific Antibody" In The Proceedings of the 77th Meetings of the Endocrine Society, p. 90.

Guillemin, Roger (1993) "Somatostatin: The Early Days" Digestion 54(suppl 1):3–6.

Harlow, Ed and David Lane (1988) Antibodies: A Laboratory Manual, Cold Spring Harbor Laboratory.

Harris, A. G. and S.P. Kokoris (1993) "Applications Therapeutiques de la Somatostatine et de Son Analogue, l'Octreotide" La Presse Medicale 22(15):724–733.

Hershberger, Ray E. et al (1994) "The Somatostatin Receptors SSTR1 and SSTR2 Are Coupled to Inhibition of Adenylyl Cyclase in Chinese Hamster Ovary Cells via Pertussis Toxin–Sensitive Pathways" Endocrinology 134(3):1277–1285.

Hoyer, Daniel et al. (1994) "Molecular Pharmacology of Somatostatin Receptors" Naunyn–Schmiedeberg's Archives of Pharmacology 350:441–453.

Hoyer, D. et al. (1995) "Classification and Nomenclature of Somatostatin Receptors" TiPS 16:86–88.

Hurst, Roger D. et al. (1993) "Use of Radiolabeled Somatostatin Analogs in the Identification and Treatment of Somatostatin Receptor–Bearing Tumors" Digestion 54(suppl 1):88–91.

(List continued on next page.)

*Primary Examiner*—Nancy A Johnson
*Attorney, Agent, or Firm*—Fulbright & Jaworski L.L.P.

[57] ABSTRACT

Peptide antigens derived from the carboxy terminus of somatostatin receptors and antibodies produced using the peptide antigens. The anti-somatostatin receptor antibodies are specific for a receptor subtype and are useful in characterizing receptor subtypes expressed by tissues.

30 Claims, 3 Drawing Sheets

OTHER PUBLICATIONS

Kimura, Nobuko (1989) "Developmental Change and Molecular Properties of Somatostatin Receptors in the Rat Cerebral Cortex" Biochemical and Biophysical Research Communications 160(1):72–78.

Kimura, Nobuko et al. (1989) "Characterization of 17–β–Estradiol–Dependent and –Independent Somatostatin Receptor Subtypes in Rat Anterior Pituitary" The Journal of Biological Chemistry 264(12):7033–7040.

Kluxen, Franz–Werner (1992) "Expression Cloning of a Rat Brain Somatostatin Receptor cDNA" Proc. Natl. Acad. Sci. USA 89:4618–4622.

Krenning, E. P. et al. (1993) "In–Octreotide Scintigraphy in Oncology" Digestion 54(suppl 1):84–87.

Kvols, L. K. et al. (1992) "The Presence of Somatostatin Receptors in Malignant Neuroendocrine Tumor Tissue Predicts Responsiveness to Octreotide" The Yale Journal of Biology and Medicine 65:505–518.

Laemmli, U. K. (1970) "Cleavage of Structural Proteins During the Assembly of the Head of Bacteriophage T4" Nature 227:680–685.

Lamberts, Steven W. J. (1993) "Validation of Somatostatin Receptor Scintigraphy in the Localization of Neuroendocrine Tumors" Acta Oncologica 32(2):167–170.

Lamberts, S. W. J. et al. (1995) "Somatostatin Receptors: Clinical Implications for Endocrinology and Oncology" in 1995 Somatostatin and its receptors. Wiley, Chichester Ciba Foundation Symposium, p. 222–239.

Lerner, Richard A. et al. (1981) "Chemically Synthesized Peptide Predicted from the Nucleotide Sequence of the Hepatitis B Virus Genome Elicit Antibodies Reactive with the Native Envelope Protein of Dane Particles" Proc. Natl. Acad. Sci. USA 78(6):3403–3407.

Le Romancer, Muriel et al. (1994) "The 86–kDa Subunit of Autoantigen Ku Is A Somatostatin Receptor Regulating Protein Phosphatase–2A Activity" The Journal of Biological Chemistry 269(26):17464–17468.

Marbach, P. et al. (1993) "From Somatostatin to Sandostatin®: Pharmacodynamics and Pharmacokinetics" Digestion 54(suppl 1):9–13.

Merrifield, R. B. (1963) "Solid Phase Peptide Synthesis. I. The Synthesis of a Tetrapeptide" Journal of the American Chemical Society 85:2149–2154.

Merrifield, R. B. et al. (1982) Synthesis of the Antibacterial Peptide Cecropin A(1–33) Biochemistry 21:5020–5031.

Meyerhoff, W. et al. (1992) "Molecular Cloning of a Somatostatin–28 Receptor and Comparison of Its Expression Pattern with that of a Somatostatin–14 Receptor in Rat Brain" Proc. Natl. Acad. Sci. USA 89:10267–10271.

Moore, William T. (1991) "Monitoring Peptide Synthesis Stepwise by Mass Spectrometry" Techniques in Protein Chemistry II, Chapter 49, pp. 511–528.

Nakabayashi, Itsuko O. and Nakabayashi, Hajime (1992) Monoclonal Antibodies to Somatostatin Receptor of Rat Brain 11(6):789–794.

O'Carroll, Anne–Marie et al. (1992) "Molecular Cloning and Expression of a Pituitary Somatostatin Receptor with Preferential Affinity for Somatostatin–28" Molecular Pharmacology 42:939–946.

Patel, Yogesh C. et al. (1994) "Expression of Multiple Somatostatin Receptor Genes in AtT–20 Cells" The Journal of Biological Chemistry 269(2):1506–1509.

Pless, J. (1993) "From Somatostatin to Sandostatin®: History and Chemistry" Digestion 54(suppl 1):7–8.

Pollak, M. et al. (1992) "Potential Role for Somatostatin Analogues in Breast Cancer: Rationale and Description of an Ongoing Trial" Metabolism 41(9)suppl 2:119–120.

Presky, David H. (1988) "Iodination of [$Tyr^{11}$]Somatostatin Yields a Super High Affinity Ligand for Somatostatin Receptors in $GH_4C_1$ Pituitary Cells" Molecular Pharmacology 34:651–658.

Prevost, Gregoire, et al. "Receptors for Somatostatin and Somatostatin Analogues in Human Breast Tumors" in Annals New York Academy of Sciences, pp. 147–154.

Reyl–Desmars, Florence (1989) "Solubilization and Immunopurification of a Somatostatin Receptor from the Human Gastric Tumor Cell Line HGT–1" The Journal of Biological Chemistry 264(31):18789–18795.

Reubi, J. C. (1990) "Detection of Somatostatin Receptors in Surgical and Percutaneous Needle Biopsy Samples of Carcinoids and Islet Cell Carcinomas" Cancer Research 50:5969–6977.

Reubi, Jean–Claude (1992) "Somatostatin Receptors in the Gastrointestinal Tract in Health and Disease" The Yale Journal of Biology and Medicine 65:493–503.

Reubi, J. C. (1992) "In Vitro Detection of Somatostatin Receptors in Human Tumors" Metabolism 41(9)Suppl 2:104–110.

Reubi, J. C. (1993) "In Vitro Detection of Somatostatin Receptors in Human Tumors"Digestion 54(suppl 1):76–83.

Reubi, Jean–Claude (1995) "Multiple Actions of Somatostatin in Neoplastic Disease" TiPS 16:110–115.

Rohrer, Lucia (1993) "Cloning and Characterization of a Fourth Human Somatostatin Receptor" Proc. Natl. Acad. Sci. USA 90:4196–4200.

Schonbrunn, Agnes and Armen H. Tashijian, Jr. (1978) "Characterization of Functional Receptors for Somatostatin in Rat Pituitary Cells in Culture" The Journal of Biological Chemistry 253(18):6473–6483.

Schonbrunn, A. et al. (1993) "Somatostatin Receptor 1 (SSR1) is Expressed in GH4C1 Pituitary Cells" In The Proceedings of the 75th Meetings of the Endocrine Society, p. 476.

Schonbrunn, Agnes et al. (1995) "Function and Regulation of Somatostatin Receptor Subtypes" in 1995 Somatostatin and its receptors. Wiley, Chichester Ciba Foundation Symposium, p. 204–221.

Taylor, John E. (1994) "Detection of Somatostatin Receptor Subtype 2 (SSTR2) in Established Tumors and Tumor Cell Lines: Evidence for SSTR2 Heterogeneity" Peptides 15(7):1229–1236.

Theveniau, Magali, et al. (1992) "Development of Antibodies Against the Rat Brain Somatostatin Receptor" Proc. Natl. Acad. Sci. USA 89:4313–4318.

Theveniau, Magali et al. (1993) "Developmental Changes in Expression of a 60–kDa Somatostatin Receptor Immunoreactivity in the Rat Brain" Journal of Neurochemistry 60(5):1870–1875.

Theveniau, Magali A. et al. (1994) "Immunological Detection of Isoforms of the Somatostatin Receptor Subtype, SSTR2" Journal of Neurochemistry 63(2): 447–455.

Van Hagen, P. M. et al. (1994) "Somatostatin and the Immune and Haematopoetic System; a Review" European Journal of Clinical Investigation 24:91–99.

Viguerie, Nathalie, et al. (1988) "Functional Somatostatin Receptors on a Rat Pancreatic Acinar Cell Line" The American Physiological Society G113–G120.

Weckbecker, G. et al. (1992) "Preclinical Studies on the Anticancer Activity of the Somatostatin Analogue Octreotide (SMS 201–995)" Metabolism 41(9)Suppl 2:99–103.

Weckbecker, G. et al. (1993) "Preclinical Studies on the Anticancer Activity of the Somatostatin Analog Octreotide (SMS 201–995)" Digestion 54(suppl 1):98–103.

Weckbecker, G. et al. (1993) "Somatostatin Analogs for Diagnosis and Treatment of Cancer" Pharmac. Ther. 60:245–264.

Yamada, Yuichiro, et al. (1992) "Somatostatin Receptors, an Expanding Gene Family: Cloning and Functional Characterization of Human SSTR3, a Protein Coupled to Adenylyl Cyclase" Molecular Endocrinology 6(12):2136–2142.

Yamada, Yuichiro, et al. (1992) "Cloning and Functional Characterization of a Family of Human and Mouse Somatostatin Receptors Expressed in Brain, Gastrointestinal Tract, and Kidney" Proc. Natl. Acad. Sci. USA 89:251–255.

Yasuda, Kazuki, et al. (1992 "Cloning of a Novel Somatostatin Receptor, SSTR3, Coupled to Adenylylcyclase" The Journal of Biological Chemistry 267(28):20422–20428.

| | Genbank# | |
|---|---|---|
| rSSTR1 | (X61630) | ..LYGFLSDNFKRSFQRILCLSWMDNAA------EEPVDYYATALKSRAYSVEDFQPENLESGGVFRNGTCASRISTL |
| mSSTR1 | (M81831) | ..LYGFLSDNFKRSFQRILCLSWMDNAA------EEPVDYYATALKSRAYSVEDFQPENLESGGVFRNGTCASRISTL |
| hSSTR1 | (M81829) | ..LYGFLSDNFKRSFQRILCLSWMDNAA------EEPVDYYATALKSRAYSVEDFQPENLESGGVFRNGTCTSRITTL |
| rSSTR2 | (M93273) | ..LYAFLSDNFKKSFQNVLCLVKV------SGAEDGERSDSKQ-DKSRLNETTETQRTLLNGDLQTSI |
| mSSTR2 | (M81832) | ..LYAFLSDNFKKSFQNVLCLVKV------SGTEDGERSDSKQ-DKSRLNETTETQRTLLNGDLQTSI |
| hSSTR2 | (M81830) | ..LYAFLSDNFKKSFQNVLCLVKV------SGTDDGERSDSKQ-DKSRLNETTETQRTLLNGDLQTSI |
| rSSTR2B | (L13033) | ..LYAFLSDNFKKSFQNVLCLVKADN--SKTGEEDTMAWV |
| mSSTR2B | (X68951) | ..LYAFLSDNFKKSFQNVLCLVKADN--SQSGAEDIIAWV |
| hSSTR2B | (L13033) | ..LYAFLSDNFKKSFQNVLCLVKVDN--SKSGEEGSCLDMIFRNNKNRKK |
| rSSTR3 | (X63574) | ..LYGFLSYRFKQGFRRIL-LRPSRRVRSQ-----EPGSGPPEKTEEEEDEEEEERREEEERRMQRGQEMNGRLSQIAQPGPSGQQQRPCT... |
| mSSTR3 | (M91000) | ..LYGFLSYRFKQGFRRIL-LRPSRRIRSQ-----EPGSGPPEKTEEEEDEEEEERRMQRGQEMNGRLSQIAQAGTSGQQPRPCTGTAKEQ... |
| hSSTR3 | (M96738) | ..LYGFLSYRFKQGFRRVL-LRPSRRVRSQ-----EPTVGPPEKTEEEDEEEEDGEESREGGKGKEMNGRVSQITQPGTSGQERPPSRVAS... |
| rSSTR4 | (M96544) | ..LYGFLSDNFRRSFQRVLCLRCCLLETTG-GAEEEPLDYYATALKSRGGPGCICPPLPCQQEPMQAEPACKRVPFTKTTTF |
| hSSTR4 | (L07061) | ..LYGFLSDNFRRSFQRVLCLRCCLLEGAG-GAEEEPLDYYATALKSKGGAGCMCPPLPCQQEALQPEPGRKRIPLTRTTTF |
| rSSTR5 | (X74828) | ..LYGFLSDNFRQSFRKVLCLRRGY------GMEDADAIEPRP-DKSGRPQATLPTRSCEANGLMQTSRI |
| hSSTR5 | (L14865) | ..LYGFLSDNFRQSFQKVLCLRKGS------GAKDADATEPRPDRIRQQQEATPPAHRAAANGLMQTSKL |

Transmembrane Domain 7

Antigenic Region

FIG. 2

SEQUENCE LISTING

```
(1) GENERAL INFORMATION:

   (iii) NUMBER OF SEQUENCES: 40


(2) INFORMATION FOR SEQ ID NO:1:

     (i) SEQUENCE CHARACTERISTICS:
          (A) LENGTH: 70 amino acids
          (B) TYPE: amino acid
          (C) STRANDEDNESS:
          (D) TOPOLOGY: linear

    (ii) MOLECULE TYPE: peptide

    (xi) SEQUENCE DESCRIPTION: SEQ ID NO:1:

Leu  Tyr  Gly  Phe  Leu  Ser  Asp  Asn  Phe  Lys
                    5                        10

Arg  Ser  Phe  Gln  Arg  Ile  Leu  Cys  Leu  Ser
                    15                       20

Trp  Met  Asp  Asn  Ala  Ala  Glu  Glu  Pro  Val
                    25                       30

Asp  Tyr  Tyr  Ala  Thr  Ala  Leu  Lys  Ser  Arg
                    35                       40

Ala  Tyr  Ser  Val  Glu  Asp  Phe  Gln  Pro  Glu
                    45                       50

Asn  Leu  Glu  Ser  Gly  Gly  Val  Phe  Arg  Asn
                    55                       60

Gly  Thr  Cys  Ala  Ser  Arg  Ile  Ser  Thr  Leu
                    65                       70


(2) INFORMATION FOR SEQ ID NO:2:

     (i) SEQUENCE CHARACTERISTICS:
          (A) LENGTH: 70 amino acids
          (B) TYPE: amino acid
          (C) STRANDEDNESS:
```

(D) TOPOLOGY: linear (ii) MOLECULE TYPE: peptide (xi) SEQUENCE DESCRIPTION: SEQ ID NO:2:

```
Leu  Tyr  Gly  Phe  Leu  Ser  Asp  Asn  Phe  Lys
                    5                        10

Arg  Ser  Phe  Gln  Arg  Ile  Leu  Cys  Leu  Ser
                    15                       20

Trp  Met  Asp  Asn  Ala  Ala  Glu  Glu  Pro  Val
                    25                       30

Asp  Tyr  Tyr  Ala  Thr  Ala  Leu  Lys  Ser  Arg
                    35                       40

Ala  Tyr  Ser  Val  Glu  Asp  Phe  Gln  Pro  Glu
                    45                       50

Asn  Leu  Glu  Ser  Gly  Gly  Val  Phe  Arg  Asn
                    55                       60

Gly  Thr  Cys  Ala  Ser  Arg  Ile  Ser  Thr  Leu
                    65                       70
```

(2) INFORMATION FOR SEQ ID NO:3:

(i) SEQUENCE CHARACTERISTICS:
(A) LENGTH: 70 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:3:

```
Leu Tyr Gly Phe Leu Ser Asp Asn Phe Lys Arg Ser Phe Gln Arg Ile
1               5                   10                  15

Leu Cys Leu Ser Trp Met Asp Asn Ala Ala Glu Glu Pro Val Asp Tyr
            20                  25                  30

Tyr Ala Thr Ala Leu Lys Ser Arg Ala Tyr Ser Val Glu Asp Phe Gln
        35                  40                  45

Pro Glu Asn Leu Glu Ser Gly Gly Val Phe Arg Asn Gly Thr Cys Thr
    50                  55                  60

Ser Arg Ile Thr Thr Leu
65                  70
```

(2) INFORMATION FOR SEQ ID NO:4:

(i) SEQUENCE CHARACTERISTICS:
(A) LENGTH: 59 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:4:

```
Leu Tyr Ala Phe Leu Ser Asp Asn Phe Lys Lys Ser Phe Gln Asn Val
1               5                   10                  15

Leu Cys Leu Val Lys Val Ser Gly Ala Glu Asp Gly Glu Arg Ser Asp
            20                  25                  30

Ser Lys Gln Asp Lys Ser Arg Leu Asn Glu Thr Thr Glu Thr Gln Arg
        35                  40                  45

Thr Leu Leu Asn Gly Asp Leu Gln Thr Ser Ile
    50                  55
```

(2) INFORMATION FOR SEQ ID NO:5:

(i) SEQUENCE CHARACTERISTICS:
(A) LENGTH: 59 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:5:

```
Leu Tyr Ala Phe Leu Ser Asp Asn Phe Lys Lys Ser Phe Gln Asn Val
1               5                   10                  15

Leu Cys Leu Val Lys Val Ser Gly Thr Glu Asp Gly Glu Arg Ser Asp
            20                  25                  30

Ser Lys Gln Asp Lys Ser Arg Leu Asn Glu Thr Thr Glu Thr Gln Arg
        35                  40                  45

Thr Leu Leu Asn Gly Asp Leu Gln Thr Ser Ile
    50                  55
```

(2) INFORMATION FOR SEQ ID NO:6:

(i) SEQUENCE CHARACTERISTICS:
(A) LENGTH: 59 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:6:

```
Leu Tyr Ala Phe Leu Ser Asp Asn Phe Lys Lys Ser Phe Gln Asn Val
1               5                   10                  15

Leu Cys Leu Val Lys Val Ser Gly Thr Asp Asp Gly Glu Arg Ser Asp
            20                  25                  30

Ser Lys Gln Asp Lys Ser Arg Leu Asn Glu Thr Thr Glu Thr Gln Arg
        35                  40                  45

Thr Leu Leu Asn Gly Asp Leu Gln Thr Ser Ile
    50                  55
```

(2) INFORMATION FOR SEQ ID NO:7:

(i) SEQUENCE CHARACTERISTICS:
(A) LENGTH: 36 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:7:

```
Leu Tyr Ala Phe Leu Ser Asp Asn Phe Lys Lys Ser Phe Gln Asn Val
1               5                   10                  15

Leu Cys Leu Val Lys Ala Asp Asn Ser Lys Thr Gly Glu Glu Asp Thr
            20                  25                  30

Met Ala Trp Val
        35
```

(2) INFORMATION FOR SEQ ID NO:8:

(i) SEQUENCE CHARACTERISTICS:
(A) LENGTH: 36 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:8:

```
Leu Tyr Ala Phe Leu Ser Asp Asn Phe Lys Lys Ser Phe Gln Asn Val
1               5                   10                  15

Leu Cys Leu Val Lys Ala Asp Asn Ser Gln Ser Gly Ala Glu Asp Ile
            20                  25                  30

Ile Ala Trp Val
        35
```

(2) INFORMATION FOR SEQ ID NO:9:

(i) SEQUENCE CHARACTERISTICS:
(A) LENGTH: 46 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:9:

```
Leu Tyr Ala Phe Leu Ser Asp Asn Phe Lys Lys Ser Phe Gln Asn Val
1               5                   10                  15

Leu Cys Leu Val Lys Val Asp Asn Ser Lys Ser Gly Glu Glu Gly Ser
            20                  25                  30

Cys Leu Asp Met Ile Phe Arg Asn Asn Lys Asn Arg Lys Lys
        35                  40                  45
```

(2) INFORMATION FOR SEQ ID NO:10:

(i) SEQUENCE CHARACTERISTICS:
(A) LENGTH: 83 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:10:

```
Leu Tyr Gly Phe Leu Ser Tyr Arg Phe Lys Gln Gly Phe Arg Arg Ile
1               5                   10                  15

Leu Leu Arg Pro Ser Arg Arg Val Arg Ser Gln Glu Pro Gly Ser Gly
            20                  25                  30

Pro Pro Glu Lys Thr Glu Glu Glu Glu Asp Glu Glu Glu Glu Glu Arg
        35                  40                  45

Arg Glu Glu Glu Glu Arg Arg Met Gln Arg Gly Gln Glu Met Asn Gly
    50                  55                  60

Arg Leu Ser Gln Ile Ala Gln Pro Gly Pro Ser Gly Gln Gln Gln Arg
65                  70                  75                  80

Pro Cys Thr
```

(2) INFORMATION FOR SEQ ID NO:11:

(i) SEQUENCE CHARACTERISTICS:
(A) LENGTH: 83 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:11:

```
Leu Tyr Gly Phe Leu Ser Tyr Arg Phe Lys Gln Gly Phe Arg Arg Ile
```

-continued

```
1               5                   10                  15

Leu Leu Arg Pro Ser Arg Arg Ile Arg Ser Gln Glu Pro Gly Ser Gly
            20                  25                  30

Pro Pro Glu Lys Thr Glu Glu Glu Glu Asp Glu Glu Glu Glu Glu Arg
        35                  40                  45

Arg Met Gln Arg Gly Gln Glu Met Asn Gly Arg Leu Ser Gln Ile Ala
    50                  55                  60

Gln Ala Gly Thr Ser Gly Gln Gln Pro Arg Pro Cys Thr Gly Thr Ala
65                  70                  75                  80

Lys Glu Gln
```

(2) INFORMATION FOR SEQ ID NO:12:

(i) SEQUENCE CHARACTERISTICS:
(A) LENGTH: 83 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:12:

```
Leu Tyr Gly Phe Leu Ser Tyr Arg Phe Lys Gln Gly Phe Arg Arg Val
1               5                   10                  15

Leu Leu Arg Pro Ser Arg Arg Val Arg Ser Gln Glu Pro Thr Val Gly
            20                  25                  30

Pro Pro Glu Lys Thr Glu Glu Glu Asp Glu Glu Glu Glu Asp Gly Glu
        35                  40                  45

Glu Ser Arg Glu Gly Gly Lys Gly Lys Glu Met Asn Gly Arg Val Ser
    50                  55                  60

Gln Ile Thr Gln Pro Gly Thr Ser Gly Gln Glu Arg Pro Pro Ser Arg
65                  70                  75                  80

Val Ala Ser
```

(2) INFORMATION FOR SEQ ID NO:13:

(i) SEQUENCE CHARACTERISTICS:
(A) LENGTH: 79 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:13:

```
Leu Tyr Gly Phe Leu Ser Asp Asn Phe Arg Arg Ser Phe Gln Arg Val
1               5                   10                  15

Leu Cys Leu Arg Cys Cys Leu Leu Glu Thr Thr Gly Gly Ala Glu Glu
            20                  25                  30

Glu Pro Leu Asp Tyr Tyr Ala Thr Ala Leu Lys Ser Arg Gly Gly Pro
        35                  40                  45

Gly Cys Ile Cys Pro Pro Leu Pro Cys Gln Gln Glu Pro Met Gln Ala
    50                  55                  60

Glu Pro Ala Cys Lys Arg Val Pro Phe Thr Lys Thr Thr Thr Phe
65                  70                  75
```

(2) INFORMATION FOR SEQ ID NO:14:

(i) SEQUENCE CHARACTERISTICS:
(A) LENGTH: 79 amino acids
(B) TYPE: amino acid (C) STRANDEDNESS:
(D) TOPOLOGY: linear (ii) MOLECULE TYPE: peptide (xi) SEQUENCE DESCRIPTION: SEQ ID NO:14:

```
Leu Tyr Gly Phe Leu Ser Asp Asn Phe Arg Arg Ser Phe Gln Arg Val
1               5                   10                  15

Leu Cys Leu Arg Cys Cys Leu Leu Glu Gly Ala Gly Gly Ala Glu Glu
            20                  25                  30

Glu Pro Leu Asp Tyr Tyr Ala Thr Ala Leu Lys Ser Lys Gly Gly Ala
        35                  40                  45

Gly Cys Met Cys Pro Pro Leu Pro Cys Gln Gln Glu Ala Leu Gln Pro
    50                  55                  60

Glu Pro Gly Arg Lys Arg Ile Pro Leu Thr Arg Thr Thr Thr Phe
65                  70                  75
```

(2) INFORMATION FOR SEQ ID NO:15:

(i) SEQUENCE CHARACTERISTICS:
(A) LENGTH: 61 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:15:

```
Leu Tyr Gly Phe Leu Ser Asp Asn Phe Arg Gln Ser Phe Arg Lys Val
1               5                   10                  15

Leu Cys Leu Arg Arg Gly Tyr Gly Met Glu Asp Ala Asp Ala Ile Glu
            20                  25                  30

Pro Arg Pro Asp Lys Ser Gly Arg Pro Gln Ala Thr Leu Pro Thr Arg
        35                  40                  45

Ser Cys Glu Ala Asn Gly Leu Met Gln Thr Ser Arg Ile
    50                  55                  60
```

(2) INFORMATION FOR SEQ ID NO:16:

(i) SEQUENCE CHARACTERISTICS:
(A) LENGTH: 62 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:16:

```
Leu Tyr Gly Phe Leu Ser Asp Asn Phe Arg Gln Ser Phe Gln Lys Val
1               5                   10                  15

Leu Cys Leu Arg Lys Gly Ser Gly Ala Lys Asp Ala Asp Ala Thr Glu
            20                  25                  30

Pro Arg Pro Asp Arg Ile Arg Gln Gln Gln Glu Ala Thr Pro Pro Ala
        35                  40                  45

His Arg Ala Ala Ala Asn Gly Leu Met Gln Thr Ser Lys Leu
    50                  55                  60
```

(2) INFORMATION FOR SEQ ID NO:17:

(i) SEQUENCE CHARACTERISTICS:
(A) LENGTH: 17 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:17:

```
Cys Leu Lys Ser Arg Ala Tyr Ser Val Glu Asp Phe Gln Pro Glu Asn
1               5                   10                  15

Leu
```

(2) INFORMATION FOR SEQ ID NO:18:

(i) SEQUENCE CHARACTERISTICS:
(A) LENGTH: 22 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:18:

```
Cys Glu Arg Ser Asp Ser Lys Gln Asp Lys Ser Arg Leu Asn Glu Thr
1               5                   10                  15

Thr Glu Thr Gln Arg Thr
            20
```

(2) INFORMATION FOR SEQ ID NO:19:

(i) SEQUENCE CHARACTERISTICS:
(A) LENGTH: 20 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:19:

```
Cys Gln Gln Glu Pro Met Gln Ala Glu Pro Ala Ser Lys Arg Val Pro
1               5                   10                  15

Phe Thr Lys Thr
            20
```

(2) INFORMATION FOR SEQ ID NO:20:

(i) SEQUENCE CHARACTERISTICS:
(A) LENGTH: 21 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:20:

```
Cys Asp Lys Ser Gly Arg Pro Gln Ala Thr Leu Pro Thr Arg Ser Cys
1               5                   10                  15

Glu Ala Asn Gly Leu
            20
```

(2) INFORMATION FOR SEQ ID NO:21:

(i) SEQUENCE CHARACTERISTICS:
(A) LENGTH: 16 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:21:

-continued

Cys Ser Gly Thr Glu Asp Gly Glu Arg Ser Asp Ser Lys Gln Asp Lys
1 5 10 15

(2) INFORMATION FOR SEQ ID NO:22:

(i) SEQUENCE CHARACTERISTICS:
(A) LENGTH: 11 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:22:

Ser Gly Thr Glu Asp Gly Glu Arg Ser Asp Ser
1 5 10

(2) INFORMATION FOR SEQ ID NO:23:

(i) SEQUENCE CHARACTERISTICS:
(A) LENGTH: 42 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:23:

Pro Val Asp Tyr Tyr Ala Thr Ala Leu Lys
5 10

Ser Arg Ala Tyr Ser Val Glu Asp Phe Gln
15 20

Pro Glu Asn Leu Glu Ser Gly Gly Val Phe
25 30

Arg Asn Gly Thr Cys Ala Ser Arg Ile Ser
35 40

Thr Leu (2) INFORMATION FOR SEQ ID NO:24:

(i) SEQUENCE CHARACTERISTICS:
(A) LENGTH: 42 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:24:

Pro Val Asp Tyr Tyr Ala Thr Ala Leu Lys
5 10

Ser Arg Ala Tyr Ser Val Glu Asp Phe Gln
15 20

Pro Glu Asn Leu Glu Ser Gly Gly Val Phe
25 30

Arg Asn Gly Thr Cys Thr Ser Arg Ile Thr
35 40

Thr Leu (2) INFORMATION FOR SEQ ID NO:25:

(i) SEQUENCE CHARACTERISTICS:
(A) LENGTH: 31 amino acids
(B) TYPE: amino acid
(C) STRANDEDNESS:

-continued (D) TOPOLOGY: linear (ii) MOLECULE TYPE: peptide (xi) SEQUENCE DESCRIPTION: SEQ ID NO:25:

```
Glu Arg Ser Asp Ser Lys Gln Asp Lys Ser
                5                   10

Arg Leu Asn Glu Thr Thr Glu Thr Gln Arg
                15                  20

Thr Leu Leu Asn Gly Asp Leu Gln Thr Ser
                25                  30

Ile
```

(2) INFORMATION FOR SEQ ID NO:26:

(i) SEQUENCE CHARACTERISTICS:
(A) LENGTH: 4 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:26:

```
Met Ala Trp Val
```

(2) INFORMATION FOR SEQ ID NO:27:

(i) SEQUENCE CHARACTERISTICS:
(A) LENGTH: 4 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:27:

```
Ile Ala Trp Val
```

(2) INFORMATION FOR SEQ ID NO:28:

(i) SEQUENCE CHARACTERISTICS:
(A) LENGTH: 14 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:28:

```
Cys Leu Asp Met Ile Phe Arg Asn Asn Lys
                5                   10

Asn Arg Lys Lys
```

(2) INFORMATION FOR SEQ ID NO:29:

(i) SEQUENCE CHARACTERISTICS:
(A) LENGTH: 43 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:29:

```
Pro Gly Ser Gly Pro Pro Glu Lys Thr Glu
                5                   10
```

-continued

Glu Glu Glu Asp Glu Glu Glu Glu Glu Arg
15 20

Arg Glu Glu Glu Glu Arg Arg Met Gln Arg
25 30

Gly Gln Glu Met Asn Gly Arg Leu Ser Gln
35 40

Ile Ala Gln (2) INFORMATION FOR SEQ ID NO:30:

(i) SEQUENCE CHARACTERISTICS:
(A) LENGTH: 43 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:30:

Pro Gly Ser Gly Pro Pro Glu Lys Thr Glu
5 10

Glu Glu Glu Asp Glu Glu Glu Glu Glu Arg
15 20

Arg Met Gln Arg Gly Gln Glu Met Asn Gly
25 30

Arg Leu Ser Gln Ile Ala Gln Ala Gly Thr
35 40

Ser Gly Gln (2) INFORMATION FOR SEQ ID NO:31:

(i) SEQUENCE CHARACTERISTICS:
(A) LENGTH: 43 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:31:

Pro Thr Val Gly Pro Pro Glu Lys Thr Glu
5 10

Glu Glu Asp Glu Glu Glu Glu Asp Gly Glu
15 20

Glu Ser Arg Glu Gly Gly Lys Gly Lys Glu
25 30

Met Asn Gly Arg Val Ser Gln Ile Thr Gln
35 40

Pro Gly Thr (2) INFORMATION FOR SEQ ID NO:32:

(i) SEQUENCE CHARACTERISTICS:
(A) LENGTH: 43 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:32:

Pro Leu Asp Tyr Tyr Ala Thr Ala Leu Lys

-continued

```
                5                   10

Ser Arg Gly Gly Pro Gly Cys Ile Cys Pro
                15                  20

Pro Leu Pro Cys Gln Gln Glu Pro Met Gln
                25                  30

Ala Glu Pro Ala Cys Lys Arg Val Pro Phe
                35                  40

Thr Lys Thr
```

(2) INFORMATION FOR SEQ ID NO:33:

(i) SEQUENCE CHARACTERISTICS:
(A) LENGTH: 43 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:33:

```
Pro Leu Asp Tyr Tyr Ala Thr Ala Leu Lys
                5                   10

Ser Lys Gly Gly Ala Gly Cys Met Cys Pro
                15                  20

Pro Leu Pro Cys Gln Gln Glu Ala Leu Gln
                25                  30

Pro Glu Pro Gly Arg Lys Arg Ile Pro Leu
                35                  40

Thr Arg Thr
```

(2) INFORMATION FOR SEQ ID NO:34:

(i) SEQUENCE CHARACTERISTICS:
(A) LENGTH: 33 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:34:

```
Asp Ala Ile Glu Pro Arg Pro Asp Lys Ser
                5                   10

Gly Arg Pro Gln Ala Thr Leu Pro Thr Arg
                15                  20

Ser Cys Glu Ala Asn Gly Leu Met Gln Thr
                25                  30

Ser Arg Ile
```

(2) INFORMATION FOR SEQ ID NO:35:

(i) SEQUENCE CHARACTERISTICS:
(A) LENGTH: 34 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:35:

```
Asp Ala Thr Glu Pro Arg Pro Asp Arg Ile
                5                   10
```

Arg Gln Gln Gln Glu Ala Thr Pro Pro Ala
15 20

His Arg Ala Ala Ala Asn Gly Leu Met Gln
25 30

Thr Ser Lys Leu (2) INFORMATION FOR SEQ ID NO:36:

(i) SEQUENCE CHARACTERISTICS:
(A) LENGTH: 16 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:36:

Leu Lys Ser Arg Ala Tyr Ser Val Glu Asp
5 10

Phe Gln Pro Glu Asn Leu
15

(2) INFORMATION FOR SEQ ID NO:37:

(i) SEQUENCE CHARACTERISTICS:
(A) LENGTH: 21 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:37:

Glu Arg Ser Asp Ser Lys Gln Asp Lys Ser
5 10

Arg Leu Asn Glu Thr Thr Glu Thr Gln Arg
15 20

Thr (2) INFORMATION FOR SEQ ID NO:38:

(i) SEQUENCE CHARACTERISTICS:
(A) LENGTH: 20 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:38:

Cys Gln Gln Glu Pro Met Gln Ala Glu Pro
5 10

Ala Cys Lys Arg Val Pro Phe Thr Lys Thr
15 20

(2) INFORMATION FOR SEQ ID NO:39:

(i) SEQUENCE CHARACTERISTICS:
(A) LENGTH: 20 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:39:

-continued

```
Asp  Lys  Ser  Gly  Arg  Pro  Gln  Ala  Thr  Leu
                    5                        10

 Pro Thr  Arg  Ser  Cys  Glu  Ala  Asn  Gly  Leu
                    15                       20


(2) INFORMATION FOR SEQ ID NO:40:

     (i) SEQUENCE CHARACTERISTICS:
          (A) LENGTH:  22 amino acids
          (B) TYPE: amino acid
          (C) STRANDEDNESS:
          (D) TOPOLOGY: linear

    (ii) MOLECULE TYPE: peptide

    (xi) SEQUENCE DESCRIPTION: SEQ ID NO:40:

Asp  Lys  Ser  Gly  Arg  Pro  Gln  Ala  Thr  Leu
                    5                        10

Pro  Thr  Arg  Ser  Cys  Glu  Ala  Asn  Gly  Leu
                    15                       20

Met  Cys
```

SOMATOSTATIN RECEPTOR PEPTIDE ANTIGENS AND ANTIBODIES

This invention was made with government support under Grant DK32234, awarded by the National Institutes of Health. The government has certain rights in the invention.

FIELD OF THE INVENTION

This invention relates to peptide antigens derived from a specific antigenic region of the carboxy terminus of a somatostatin receptor; to somatostatin receptor subtype-specific antibodies induced by the peptide antigens, and to immunological methods using somatostatin receptor subtype-specific antibodies for determining the presence and distribution of the somatostatin receptor subtype(s) in a tissue sample and for the isolation and purification of somatostatin receptor protein(s).

BACKGROUND OF THE INVENTION

Somatostatin and Its Clinical Uses:

Somatostatin is a polypeptide having numerous physiological and pathological actions associated with the regulation of hormone, neurotransmitter and exocrine secretion as well as cell growth and differentiation. These actions of somatostatin are mediated by high affinity plasma membrane receptors in responsive cells.

Somatostatin receptors are present in many human cancers including pituitary adenomas, gastroenteropancreatic tumors and breast and prostate carcinomas. Hypersecretion of hormone by secretory tumors can be controlled by administration of a somatostatin analog which binds to and activates a somatostatin receptor. For example, when treated in vitro with the somatostatin analog octreotide, most receptor-expressing tumors respond with decreased hormone secretion and growth, however, some tumor cells react to this analog with stimulated growth. (Lamberts et.al., 1995, *Ciba Foundation Symposium* 190: *Somatostatin and its Analogs p.* 222–239.)

Somatostatin receptor-positive tumors may be visualized by administration of a labeled analog of somatostatin and determining the localization of the label. Discrepancies in binding studies using various somatostatin analogs originally demonstrated the presence of somatostatin receptor subtypes in tumors. Specific knowledge of the somatostatin receptor subtype present in a tumor is required to determine if a specific analog such as octreotide would be of therapeutic or diagnostic value in the treatment or localization of a specific patient's tumor.

Somatostatin Receptors:

Somatostatin interacts with specific membrane receptors to initiate a cellular response. Somatostatin receptors belong to a class of G-protein associated receptors having similar predicted three-dimensional structures consisting of seven transmembrane domains bridged by extracellular and intracellular loops. The predicted structure of the human sst2 receptor is shown in FIG. 1.

The somatostatin receptor family includes at least six distinct receptor subtypes encoded by five different genes, one of which generates two splice variant mRNAs. Gene sequences encoding human, rat, and, in some cases mouse somatostatin receptor (sst receptor) subtypes 1, 2, 2b, 3, 4 and 5 have been published in the literature (Bruns et al., *Ann. NY Acad. Sci.,* 733:138–146, 1994 and references cited therein). FIG. 2 shows deduced amino acid sequences of the carboxy terminus of each known receptor subtype beginning at the carboxy terminal end of the seventh putative membrane-spanning domain and extending intracellularly. As shown, there is high homology between species within each receptor subtype, but little homology between receptor subtypes.

The basic and clinical study of somatostatin receptors as well as other seven transmembrane domain receptors has been hampered by the inability to generate specific, high affinity receptor antibodies. Such antibodies are essential for the rapid isolation of receptor proteins for biochemical studies, (e.g., by immunoprecipitation), and for efficient identification and quantification of receptors in tissues and cells, (e.g., by immunocytochemistry and Western blot methods).

There are many reports describing production of anti-peptide antibodies to different regions of G-protein coupled hormone receptors. These antibodies vary markedly in their ability to bind the receptor in its native or denatured form, with many having such low affinity for the receptor that they are not practically useful. No overall strategy for identifying a useful peptide antigen from a somatostatin receptor has been successful.

Antibodies to somatostatin binding proteins:

Purified receptor protein and fragments have been postulated as antigens to generate anti-somatostatin receptor antibodies. (European Patent Appln. EP92105164.5 to Eppler; U.S. Pat. No. 5,331,094.) However, to date no such antibody has been generated and shown to bind true G-protein coupled somatostatin receptors with high affinity and with the ability to discriminate between receptor subtypes.

Antibodies against somatostatin binding proteins which are unrelated to the seven transmembrane domain somatostatin receptor have been generated. (Theveniau et.al., *J.Neurochem.*63:447–455, 1994; LeRomancer et.al., *J.Biological Chem.* 269:17464–68, 1994; Reyl-Desmars et.al., *J. Biological Chem.* 264:18789–95, 1989; Theveniau et.al., *PNAS* 89:4314–4318, 1992; Nakabayashi et.al, *Hybridoma* 11:789–794, 1992.) In one report, a 90 kDa somatostatin binding protein was isolated from a gastric cell line (Reyl-Deymars et al., *J. Biol. Chem.* 264:18789–18795, 1989) using a monoclonal antibody prepared to a partially purified, membrane protein preparation. LeRomancer et al. subsequently cloned the 90 kDa protein antigen and showed that it was unrelated to the seven-transmembrane domain somatostatin receptor family. A functional role for this somatostatin binding protein in somatostatin signaling has not been demonstrated.

Theveniau et al, (Proc. Natl. Acad. Sci. 89:4314–4318 1992), described the production of polyclonal antibodies to a size-fractionated preparation of solubilized brain membrane proteins. The resulting antiserum was microfractionated by elution from immunoblots of size fractionated brain proteins. One of the antiserum fractions contained antibodies which could precipitate a somatostatin binding activity with low efficiency (<2%) and also bound a 60 kDa protein on immunoblots. This putative "somatostatin receptor antibody" was later used by these investigators to localize a "receptor antigen." (Theveniau et al., *J Neurochem.* 60:1870–1875, 1993.) The recited antibodies do not bind any of the known seven-transmembrane domain somatostatin receptors, as shown in Theveniau et al, 1993. Moreover, the protein recognized by this antibody has never been isolated, cloned, or sequenced. Thus, any relationship of the protein recognized by this antibody to the known somatostatin receptor subtypes is unknown.

Nakabayashi et al described the production of monoclonal antibodies against a crude preparation of soluble rat brain membranes. The selected antibodies partially inhibited somatostatin binding to soluble brain proteins and also inhibited somatostatin binding to a 100 kDa protein in non-denaturing gels. Antibody binding specificity for somatostatin receptors, binding affinity, and ability to directly bind and/or discriminate between receptor subtypes was not disclosed. The paper provides no evidence that the antibodies actually bind directly to any of the known seven-transmembrane domain somatostatin receptor subtypes.

Antibodies to somatostatin receptors:

It has been proposed that antibodies could be raised against cloned sst receptors or expressed fragments thereof (e.g., Bell et al., WO 93/13130). However, to date, no such antibodies have been reported and shown to recognize and discriminate between somatostatin receptor subtypes. Several laboratories have generated antibodies to polypeptides having sequences derived from portions of the cloned somatostatin sst2 receptor. Patel et al (*J. Biological Chem.,* 269:1506–1509, 1994.) generated antibodies against a nine amino acid peptide corresponding to the extracellular amino-terminal segment containing residues 35–42 of the human sst2 receptor. Although the resulting antibodies partially inhibited the binding of somatostatin to rat brain and pituitary cell membranes, they were not shown to immunoprecipitate any receptor protein. Further, the authors did not demonstrate any inhibition of binding that was specific for the sst2 receptor subtype. In Western blots, the antibody of Patel et al. recognized a protein of approximately 72 kDa. However, the authors did not show immunostaining specific for the sst2 subtype. Moreover, the intensity of the immunostaining was not shown to be proportional to receptor density, in fact, the weakest staining was observed in sst2 receptor-expressing COS cells which should have contained the highest receptor concentration of the cells tested. Therefore, the reference does not teach or suggest any specificity of this antiserum for different sst receptor subtypes.

Theveniau et al., (*J. of Neurochemistry* 63:447–455, 1994) generated antibodies against two different peptides with sequences derived from the sst2 receptor, one from the predicted third extracellular loop (2e3) and the other from the predicted C-terminal cytoplasmic tail of the receptor (2i4) (See FIG. 1). The 2e3 antibody did not specifically immunoprecipitate the ligand-receptor complex from CHO cells expressing the sst2 receptor. The 2e3 antibody was shown to detect a 148 kDa protein in rat brain, rat pituitary, and rat Ar4-2J cells. However, the somatostatin receptors normally found in these cells and tissues have previously been shown to have substantially lower molecular weights by photoaffinity labeling. The apparent molecular weight of Ar4-2J cell somatostatin receptors is 75–80 kDa (Brown, P. J., *J. Biol. Chem.* 265:17995–18004, 1990; Viguerie, N., *Am. J. Physiol.* 255:G113–G120, 1988). The molecular weight of rat pituitary somatostatin receptors varies between 82 kDa and 94 kDa (Kimura, *J. of Biol. Chem.* 264:7033–7040, 1989). The molecular weight of rat brain somatostatin receptors is approximately 71 kDa (Kimura et al., *Biochem. Biophys. Res. Commun.* 160:72–78, 1989). Moreover, somatostatin receptors normally migrate as broad bands on SDS polyacrylamide gels, as has been observed for other glycosylated seven-transmembrane domain receptors (above references). In contrast, the 148 kDa band recognized by the 2e3 antiserum was very sharp. Both because of its uncharacteristic molecular weight and because of its unusual migration pattern on SDS-PAGE, the 148 kDa protein detected by the 2e3 antibody is unlikely to represent the sst2 receptor.

The 2i4 antibody of Theveniau et al. immunoprecipitated 10–15% of solubilized sst2 receptors prepared from CHO cells expressing recombinant sst2 receptors, but was unable to detect any specific protein in immunoblots. The affinity and specificity of this antibody was not disclosed in the reference, however, very high serum concentrations (20 μl) were used to achieve the modest immunoprecipitation reported. In studies that will be described below, antibodies were prepared against a larger peptide antigen which included the Theveniau 2i4 peptide. This larger peptide antigen was expected to have greater antigenicity than the 2i4 peptide and to produce antibodies of higher specificity for the sst2 receptor. However, this larger peptide was unable to induce antibodies having high affinity and specificity for the sst2 receptor (see Example 2).

In European patent application EP 92105164.5, Eppler purports to have raised an antibody against an eight amino acid peptide from the carboxy terminus of the sst2 receptor. Antisera from immunized animals was shown to detect purified sst2 receptor protein on a Western blot. However, the antiserum also bound to the enzyme, Endo F, which was used to deglycosylate the receptor protein and which was the only other protein in the sample. Therefore, the antibody cannot be said to have specificity for sst receptors. Moreover, there was no indication that the antibody had the sensitivity necessary to detect sst receptors in a heterogenous, unpurified preparation.

Cloned Somatostatin Receptors:

Bell et al, WO 93/13130, discloses the gene sequence encoding seven transmembrane domain somatostatin receptors sst1 and sst2 and recites methods for producing antibodies to the cloned receptors using recombinant proteins or protein fragments derived from the DNA sequence. This reference fails to identify any particular sequence of the cloned sst1 or sst2 receptor which would successfully induce antibodies, and importantly, does not disclose or suggest any sequence of the cloned receptors as inducing antibodies having the ability to recognize a specific receptor subtype.

Somatostatin receptor subtypes:

The ability to discriminate between somatostatin receptor subtypes in a sample tissue is critical to the development and use of somatostatin analogs in diagnostic and therapeutic methods targeting a specific receptor subtype. For example, the somatostatin analog OCTREOTIDE® (also known as SANDOSTATIN® or SMS 201-995), interacts with the sst2, and sst5 receptors, and to some extent with the sst3 receptor, but not with sst1 and sst4 receptors. This analog has been approved for clinical use in the treatment of certain tumors which express sensitive sst receptors. (Pless, *J. Digestion,* 54 (Suppl. 1):7–8, 1993) To date there is no quick, easy, and precise method to determine if a tissue or tumor sample expresses a receptor subtype which can be effectively treated by an analog such as SANDOSTATIN or any other receptor subtype-specific somatostatin analog.

It would be very useful to provide antibodies for efficient and predictable screening of sample tissues to identify those expressing specific somatostatin receptor subtypes. Such antibodies must have a high affinity and specificity for a particular receptor subtype and be capable of specifically recognizing the seven transmembrane domain somatostatin receptor subtype by either immunocytochemical staining, immunoblotting, immunoprecipitation, on an ELISA-type assay.

SUMMARY OF THE INVENTION

A region of the somatostatin receptor has been identified at the receptor's carboxy terminus extending intracellularly from the seventh putative transmembrane domain of the receptor which region contains a peptide antigen capable of inducing high affinity, high specificity, anti-somatostatin receptor antibodies capable of recognizing and distinguishing between somatostatin receptor subtypes. The specific region is a 10–30 amino acid sequence, preferably a 15–25 amino acid sequence, positioned from approximately 20 residues to approximately 70 residues downstream from the seventh putative transmembrane domain as it exits the membrane and projects intracellularly. In general, this region begins 10 to 15 residues after the putative palmitoylation site, within the C-terminal region of the receptor, (10–15 residues after the first cysteine residue positioned at about 12 amino acids from the C-terminal end of the seventh putative transmembrane domain), and extends approximately 50 residues toward the carboxy terminus. This specific antigenic region of the receptor is diagrammatically shown as those sequences contained within the hatched box in FIG. 2. Exemplary synthetic peptides which have been used to produce specific anti-somatostatin receptor subtype antibodies are those contained within the smaller shaded boxes in FIG. 3, and shown in Table 1, infra. Using these proven subtype-specific antigens, additional subtype-specific antigens, e.g., from other receptor subtypes or species, may be designed and screened for their ability to generate somatostatin receptor subtype-specific antibodies. Antibodies raised against the peptide antigens of the present invention specifically, and with high affinity, bind a somatostatin receptor subtype and permit identification of somatostatin receptor subtype(s) present in a tissue sample by immunological methods, including immunoblot, immunocytochemical or immunoprecipitating analyses. Identification of individual somatostatin receptor protein(s) is crucial for efficient development of subtype-specific somatostatin analogs and for their diagnostic and therapeutic use. The invention also provides methods for isolating specific somatostatin receptor proteins from both recombinant and non-recombinant sources by immunoaffinity purification using the receptor specific antibodies.

BRIEF DESCRIPTION OF THE FIGURES

FIG. 2 shows the amino acid sequences of human, rat, and mouse somatostatin receptors, beginning at the end of the receptor's seventh putative transmembrane domain and extending towards the receptor's intracellular carboxy terminus. The subtype-specific antigenic region of the receptor's sequence is indicated by the hatched box. The boxed portions of the sequences shown for rSSTR1, mSSTR1, hSSTR1, rSSTR2, mSSTR2, hSSTR2, rSSTR2B, mSSTR2B, hSSTR2B, rSSTR3, mSSTR3, hSSTR3, rSSTR4, hSSTR4, rSSTR5, and hSSTR5 represent SEQ ID NO. 1–16, respectively.

DETAILED DESCRIPTION OF THE INVENTION

Figure 1:
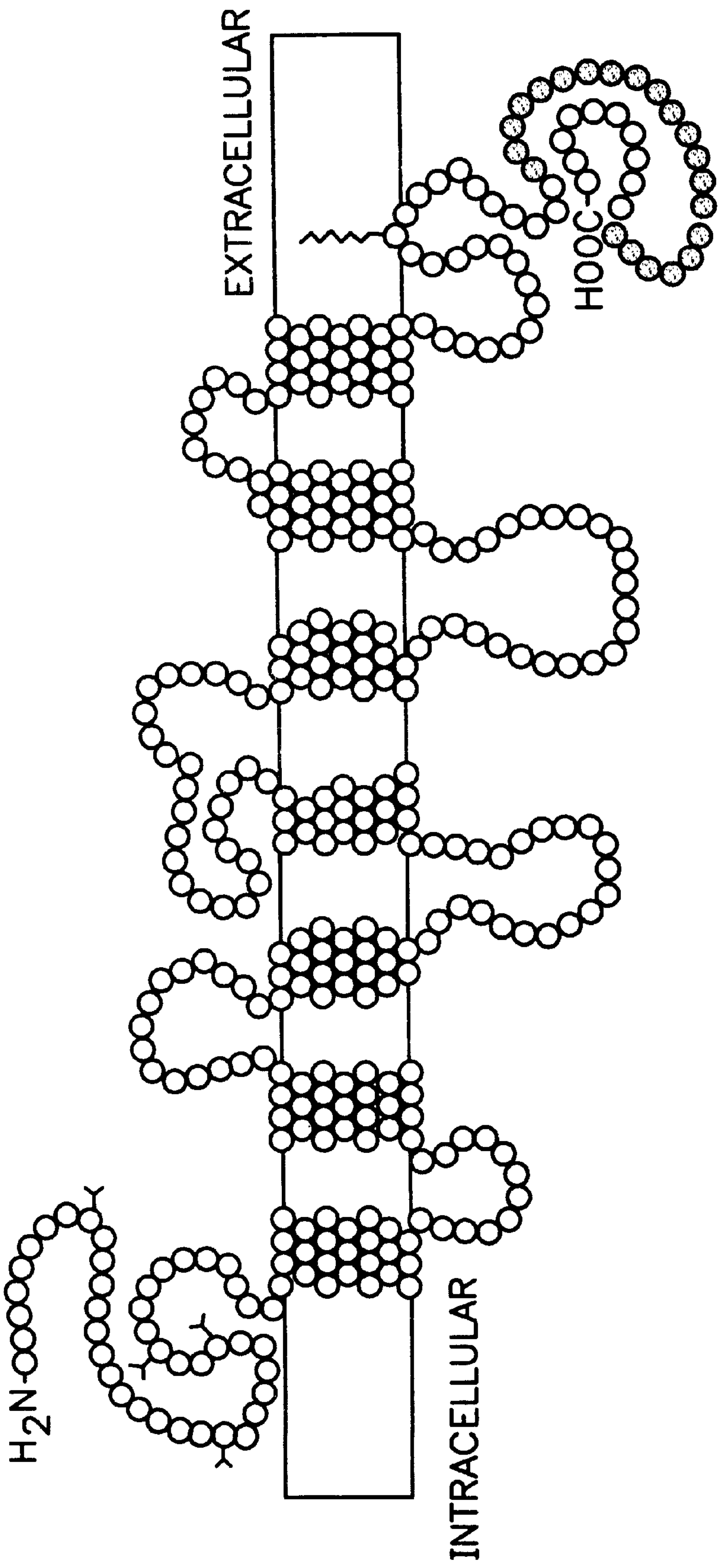
FIG. 1 is a diagrammatic representation of the seven transmembrane domain somatostatin receptor, specifically showing the amino acid sequence of the human sst2 receptor. A specific antigenic peptide of the carboxy terminus useful for inducing sst2 receptor-specific antibodies is indicated by the shaded amino acid sequence.
Figure 3:
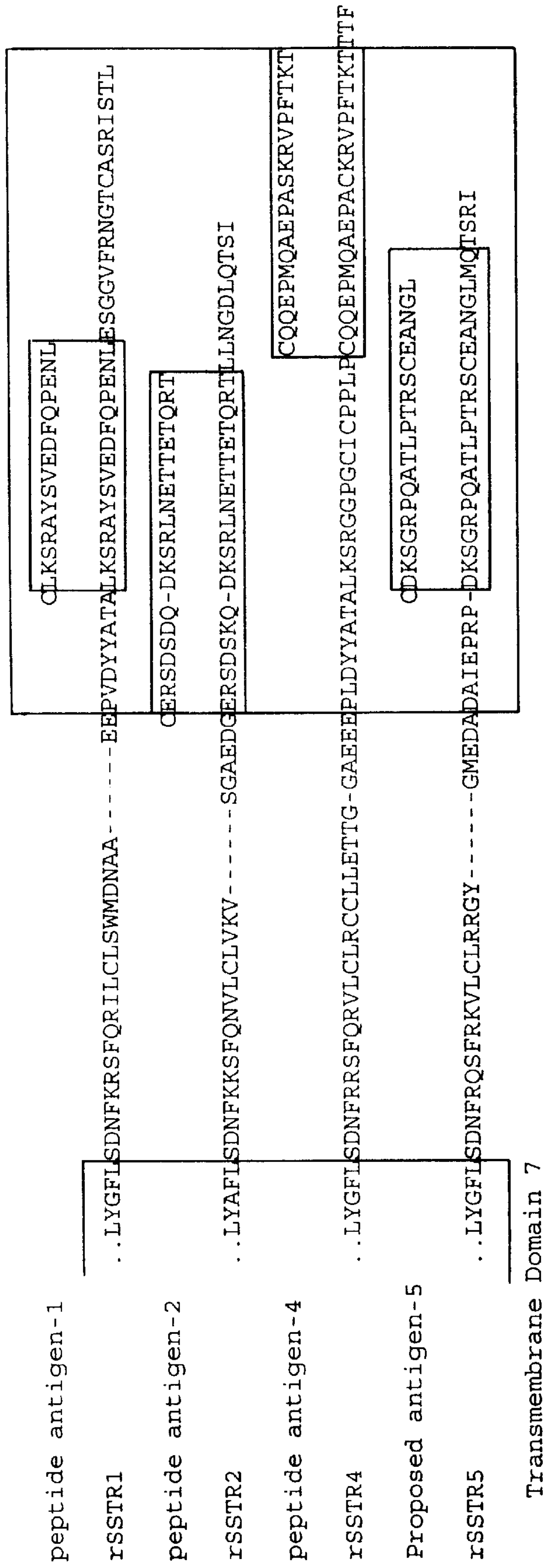
FIG. 3 shows the amino acid sequences of the rat somatostatin receptors, beginning at the end of the putative seventh transmembrane domain and extending to the intracellular carboxy terminus. The subtype-specific antigenic region of the receptor is shown in the hatched box, and representative antigenic peptides which induce high affinity receptor subtype specific antibodies are shown in the smaller, shaded boxes. An asterisk indicates the position of the conserved cysteine which is a potential palmitoylation site. The sequences above the rSSTR1, rSSTR2, rSSTR4, and rSSTR5 sequences represent SEQ ID Nos. 17–20, respectively. The boxed portions of sequences rSSTR1, rSSTR2, and rSSTR4 represent SEQ ID Nos. 36–38, respectively. The boxed portion of the sequence above the rSSTR5 sequence represents SEQ ID NO. 39, while the boxed portion of the rSSTR5 sequence represents SEQ ID NO. 40.

Selected Epitope:

The present invention encompasses an antigenic region of a somatostatin receptor positioned in the carboxy terminal region approximately 20–75 amino acids downstream of the putative seventh transmembrane domain, as shown by the boxed sequences of FIGS. 2 and 3 (SEQ ID NOS. 17–20, 23–40). The preferred antigenic peptide is a sequence of at least 10 amino acids and more preferably at least 15 amino acids. In general, the preferred peptide antigen is a sequence of 30 or less amino acids, and most preferably is a sequence of 15–30 amino acids. The peptide antigen is a sequence of the somatostatin receptor, positioned near the carboxy terminus beginning approximately 10 residues after the first intracellular cysteine (C), after the seventh putative transmembrane domain. In sstr2A, this cysteine is positioned about 12 amino acids downstream of the F-L-S- sequence (see FIGS. 2 and 3). Most preferably, the antigenic peptide is an amino acid sequence shown within the hatched box of FIG. 2 (SEQ ID NOS. 23–35) and most preferably is one of the amino acid sequences shown in the shaded boxes of FIG. 3 (SEQ ID NOS: 17–20, and 36–40) or a functional derivative thereof.

The term "functional derivative" is meant to include functionally comparable peptides derived from the same region of a seven-transmembrane domain somatostatin receptor as the boxed sequences of FIGS. 2 and 3, and having a similar ability to induce subtype-specific anti-somatostatin receptor antibodies. Such a functional derivative may be a similarly positioned peptide of another species sst receptor or a peptide derived from the sequences shown in the shaded boxes of FIG. 3 having substitutions, additions or deletions of amino acids, provided the derivation does not alter the ability of the peptide antigen to induce subtype-specific antibodies. The peptide antigen of this invention includes those peptides whose amino acid sequence is shifted within a few amino acids upstream or downstream of the antigenic peptides shown in the shaded boxes of FIG. 3, as well as those peptides having conservative amino acid changes such as substitutions, additions, or deletions of amino acids, which shift or changes do not significantly affect the ability of the peptide antigen to induce antibodies which bind to a specific receptor subtype with high affinity and specificity. For example, adding a cysteine or other coupling group to the peptide antigen's sequence provides a functional derivative of the antigen which facilitates its coupling to a carrier protein. A functional derivative peptide antigen of this invention also includes those peptides having nonconservative amino acid changes from the amino acid sequences shown in the shaded boxes of FIG. 3, which changes correspond to mutant somatostatin receptors associated with disease states and which peptides can induce antibodies which bind the specific mutant somatostatin receptors.

For sstr1 and sstr2A, the rat, mouse, and human sequences are virtually identical in the region of the preferred peptide antigen. For sstr4 and sstr5, the rat, mouse, and human sequences differ by several amino acids. To obtain the highest affinity possible for the sstr4 and sstr5 antigens, separate antibodies should be generated against the appropriate comparable peptide from each species.

TABLE 1

| SEQ ID NO: | receptor | PEPTIDE ANTIGEN |
|---|---|---|
| 17 | *sstr1* | CLKSRAYSVEDFQPENL |
| 18 | *sstr2A* | CERSDSKQDKSRLNETTETQRT |
| 19 | *sstr4* | CQQEPMQAEPASKRVPFTKT |
| 20 | *sstr5* | CDKSGRPQATLPTRSCEANGL |

Antibody Production:

A selected peptide for antibody production is synthesized by conventional methods, for example by solid-phase chemical synthesis (e.g. R. B. Merrifield, Science 85:2149–2154, 1963) or by recombinant technology (e.g. using bacterially expressed polypeptides). For increased antigenicity, synthetic peptides are chemically coupled to a carrier protein whereas recombinant peptides may be generated as fusion proteins. The antigen peptides are then screened for their ability to induce subtype-specific anti-somatostatin receptor antibodies by conventional methods, for example, by the antigen's ability to induce antibodies which specifically bind a somatostatin receptor subtype and not other subtypes as determined in an immunoprecipitation, immunoblot or immunocytochemical assay.

The peptide antigens of the present invention are used to generate somatostatin receptor subtype-specific antibodies, using conventional techniques. Preferably, for synthetic peptides, the peptide antigen includes either an N-terminal cysteine or a lysine to assist in conjugation of the peptide to a carrier protein such as keyhole limpet hemocyanin using m-maleimidobenzoyl-N-hydroxysuccinimide ester or glutaraldehyde. Alternatively, the antigen is synthesized as a fusion protein with an unrelated protein to allow its ready purification from other bacterial proteins and to increase its antigenicity. For examples see, *Antibodies, a Laboratory Manual*, Ed Harlow and David Lane, eds., Cold Spring Harbor Laboratory, 1988.

Anti-Somatostatin Receptor Screening Methods:

The peptide antigen, preferably with an adjuvant, (e.g., complete Freund's adjuvant), is used to immunize a host animal, (e.g., rabbits, goats, or mice). Generally, after the first injection, subsequent immunizing doses of antigen are given with incomplete Freund's adjuvant. Antibody titer is monitored, for example, by monthly bleeds, and anti-sera are screened for the presence of anti-peptide and anti-receptor antibodies.

Administration of the antigen for immunization is accomplished by conventional methods, for example, by intradermal, subcutaneous, or intramuscular injection, or by another conventional mode. Intradermal injection is preferred. The dose of peptide antigen administered varies with the specific peptide and with the animal host. The first injection generally contains a greater mass of peptide than subsequent boosts. For example, a first injection in rabbits may contain 200–400 $\mu$g of coupled peptide in complete Freund's adjuvant, whereas subsequent injections may contain 100–200 $\mu$g in Freund's incomplete adjuvant. Injections are scheduled at approximately monthly intervals, and rabbits bled about 7 to 14 days after each boost.

Antisera produced in the host animals are initially screened for the presence of anti-peptide antibodies, e.g., by ELISA. In general, the peptide antigen is first applied to multiwell assay plates, and diluted antisera are incubated with the antigen for a time sufficient to permit antibody-antigen binding. After washing away excess antibodies, the amount of antibody-antigen complex formed is determined using a marker system, e.g., a second antibody linked to a color-producing enzyme, a fluorescent molecule, or a radioactive label.

Positive antisera are further screened for binding to a specific receptor subtype, e.g., by measuring antibody immunoprecipitation of a particular somatostatin receptor or by dot blot, Western blot, or immunocytochemical staining analysis. For example, membranes are prepared from cells transfected with an expression plasmid encoding a specific somatostatin receptor subtype and incubated with a radiolabelled somatostatin receptor ligand. Following this binding reaction, the membrane proteins are solubilized and soluble proteins are incubated with the antisera to be screened. Antibodies are then adsorbed to Protein-A-Sepharose, centrifuged, and the amount of ligand-receptor complex present in the immunoprecipitate is quantitated.

In an alternative screening method, membranes prepared from cells expressing a specific somatostatin receptor subtype are solubilized and subjected to polyacrylamide gel electrophoresis (PAGE). The separated proteins are transferred to nitrocellulose and probed with antisera. The antibodies of the instant invention each recognize a specific somatostatin receptor subtype and do not show significant cross-reactivity with other receptor subtypes.

Use of Antibodies to classify tissue:

The subtype-specific anti-somatostatin receptor antibodies of the present invention are used to classify a tissue or tumor as expressing a particular somatostatin receptor subtype(s). As a diagnostic tool, this classification identifies a particular somatostatin analog which can be effectively used in further diagnosis (e.g., scintigraphy or imaging of tumors) (Lamberts et al., *Acta Oncologia,* 32:167–170, 1993; Kvols et al., *Yale J Biology & Med.,* 65:505–518, 1992) or in therapeutic applications (e.g., to inhibit proliferation of a target tissue or to inhibit hormone secretion by a target tissue) (Weckbecher et al., *Digestion,* 54(Suppl. 1) 98–103, 1993). Knowing the subtype of the somatostatin receptor expressed by a tissue or tumor, an analog known to bind and interact with that receptor as an agonist or antagonist can be selected and used.

Antibodies of the present invention are used in immunological techniques such as immunocytochemical staining and immunoblotting to correlate the presence of a specific receptor subtype with a known disease. For example, some breast and prostate tumors are known to express somatostatin receptors. Identification of the specific receptor subtype (s) expressed by a patient's tumor can be used to target a specific therapy.

The antibodies of the present invention may be monoclonal or polyclonal, and are produced according to conventional immunological methods. (See, for example, *Antibodies, A Laboratory Manual*, Harlow, E. and Lane, D., Cold Spring Harbor Laboratory, 1988.) The antibodies may be used alone or in combination, e.g., in panels, to screen a tissue for the presence of specific somatostatin receptor subtypes. In a preferred embodiment, an immunological assay kit is provided, which kit contains a plurality of anti-somatostatin receptor antibodies, each antibody recognizing a specific receptor subtype.

Use of antibody for receptor isolation:

The subtype specific anti-somatostatin receptor antibodies of the present invention are used in standard immunoaffinity purification protocols to purify somatostatin receptors or receptor fragments from tissues or recombinant prokaryotic or eukaryotic cells expressing high levels of receptor. The receptors or receptor fragments so purified can be used for generation of antibodies to the intact receptor protein or fragments thereof or for other applications requiring high concentrations of pure receptor protein.

EXAMPLES

Example 1

Identification of an antigenic peptide of the sst1 receptor Selection of Peptide Sequence:

The deduced amino acid sequence of the cloned sst1 receptor was analyzed to select an optimal antigenic site. Specifically, the variable internal carboxy terminal region of the receptor protein was examined for amino acid sequences having high hydrophillicity. The chosen peptide was a 15 amino acid polypeptide corresponding to amino acids 358–372 of the sst1 receptor, near the carboxy terminus. The selected sequence is unique to somatostatin receptor subtype 1 and is completely conserved between the rat, mouse, and human receptors:

[C]LKSRAYSVEDFQPENL (Seq. ID No. 17)

The peptide was synthesized with an N-terminal cysteine using an Applied Biosystems ABI peptide synthesizer (Model 430A) using t-BOC/Benzyl solid-phase methodology (Merrifield et al., 1982, *Biochemistry* 21:5020–5031.) Peptide structure was confirmed by fast atom bombardment mass spectrometry according to the methods described in Moore et al., 1991, *In: Techniques in Protein Chemistry II*, J. Villafranca, Ed., Academic Press, San Diego, Calif., pages 511–527. Purity was determined by reverse phase HPLC using conventional methods. The synthesized peptide had the expected mass of 1886 daltons and was greater than 95% pure.

Antibody Production:

The selected peptide was conjugated to keyhole limpet hemocyanin (KLH) through the N-terminal cysteine using m-maleimidobenzoyl-N-hydroxysuccinimide (MBS), as described in Lerner et al., 1981, *Proc. Nat. Acad. Sci. USA,* 78:3403–3407. Specifically, 4 mg KLH in 320 $\mu$l Dulbecco's phosphate buffered saline was reacted for 30 minutes with 28 $\mu$l of MBS, freshly dissolved in dimethylformamide (80 mM). Following purification on a Sephadex column, those fractions containing KLH-MBS were mixed with 5 mg of peptide in 1 ml of 0.1 M phosphate buffer and incubated for 3 hours at room temperature.

For initial injection, the conjugated peptide (~400 $\mu$g) was emulsified with an equal volume of Freund's complete adjuvant and injected intradermally into New Zealand white male rabbits (Ray Nichols, Lumberton, Tex.). One month after the initial injection, the rabbits were boosted with ~200 $\mu$g peptide emulsified with an equal volume of incomplete Freund's adjuvant. Booster injections were repeated with ~100–200 $\mu$g coupled peptide at monthly intervals and the rabbits were bled 7–14 days after each boost. Each bleed was screened for positive antisera by enzyme-linked immunosorbent assay (ELISA). Positive antibody was detected following the first boost in each test animal.

Screening of Antisera by ELISA:

To measure the apparent binding affinity of the antiserum for peptide antigen, 25–50 ng peptide was adsorbed to each well of a 96 well plate at 4° C. After saturating binding sites with 1% gelatin for two hours, plates were incubated for two hours at room temperature with 100 $\mu$l of 1:10,000 dilution of the antisera and varying concentrations of peptide antigen. After washing, the wells were incubated with horseradish peroxidase-conjugated goat anti-rabbit IgG (1:3000) for one hour. Plates were then washed and incubated thirty minutes with hydrogen peroxide and 2,2'-azino-di-[3-ethylbezthiazoline-6-sulfonic acid], diluted according to the manufacturer's instructions (Bio-Rad, Hercules, Calif.). The reaction was stopped with 100 $\mu$l of 2% oxalic acid and the bound antibody in each well was visualized by measuring absorbance at 405 nm.

As shown below in Table 2, the antiserum (R1-201) bound the sst1 receptor peptide antigen with high affinity, e.g., at a dilution of 1:10,000, $ED_{50}$=18±1 nM.

TABLE 2

BINDING OF ANTISERUM R1-201 TO *sst1* receptor-peptide

| Competing peptide (M) | A405* R1-201 |
|---|---|
| 0 | 1.46 |
| $1 \times 10^{-10}$ | 1.47 |
| $3 \times 10^{-10}$ | 1.46 |
| $1 \times 10^{-9}$ | 1.40 |
| $3 \times 10^{-9}$ | 1.23 |
| $1 \times 10^{-8}$ | 0.969 |
| $3 \times 10^{-8}$ | 0.660 |
| $1 \times 10^{-7}$ | 0.429 |
| $3 \times 10^{-7}$ | 0.252 |
| $1 \times 10^{-6}$ | 0.200 |
| $1 \times 10^{-5}$ | 0.097 |
| O (pre Immune) | 0.037 |

*Values are the mean of 4 replicates.

Screening of Antisera by Immunoprecipitation:

The antisera induced by the antigenic peptide were first analyzed for their ability to precipitate specific somatostatin-receptor binding activity. Secondly, the ability of each antiserum to immunoprecipitate photoaffinity labeled somatostatin receptor protein was determined.

To generate preparations containing specific somatostatin receptors, Chinese hamster ovary cells (CHO-K1) stably transfected with genes encoding rat sst1 or sst2 receptor were obtained from Dr. Stork of the Vollum Institute in Portland, Oreg. (Hershberger et al., *Endocrinology,* 134:1277–1285, 1994), CHO-K1 cells stably transfected with the sst4 receptor were obtained from Drs. Bruno and Berelowitz of SUNY, Buffalo, N.Y., (Bruno et al., *PNAS,* 89:11151–11155, 1992), and CHO-K1 cells stabily transfected with sst3 receptor were obtained from Dr. Patel of McGill University, Montreal, Quebec, Canada (Panetta et al., *Mol. Pharmacol.* 45:417–427, 1994). Untransfected CHO-K1 cells do not express detectable somatostatin receptors.

The immunoprecipitation procedure involves preincubation of somatostatin receptor-containing plasma membranes with radiolabelled ligand, solubilization of the somatostatin receptor-ligand complexes in an active state, quantitation of the amount of the soluble complex by precipitation with polyethylene glycol (PEG), and specific precipitation of the receptors with the test antisera.

Cell membranes from transfected CHO cells were prepared and stored according to published procedures (P. J. Brown et al., 1990, *J. Biol. Chem,* 265:17995–18004). Briefly, cells from either monolayer or suspension cultures were collected, washed with phosphate-buffered saline (10 mM $Na_2PO_4$, 150 mM NaCl, pH 7.4) and homogenized at 4° C. in Tris buffer (10 mM TrisCl, 2 mM $MgCl_2$, 2 mM EDTA, 0.5 mM freshly prepared phenylmethylsulfonyl fluoride, pH 7.6). Following centrifugation at 500×g for 10 minutes, the supernatant was collected and centrifuged again at 10,000×g for 30 minutes. The membrane pellet was then resuspended in gly—gly buffer (20 mM glycylglycine, 1 mM $MgCl_2$, 250 mM sucrose, pH 7.2) and stored at −70° C.

The somatostatin analogs, [$Tyr^{11}$]SRIF and the photoactive somatostatin analog [$Tyr^{11}$, ANB-$Lys^4$]SRIF were radiolabelled with $Na^{125}I$ using Chloramine-T and the iodinated peptides were purified by reverse-phase HPLC to a specific activity of 2200 Ci/mmole (P. J. Brown et al., *J. Biol. Chem,* 1990, 265:17995–18004; Presky and Schonbrunn, 1988, *Mol. Pharm.,* 34:651–658).

Binding reactions were performed according to published procedure (P. J. Brown et al., *J Biol. Chem,* 1990, 265:17995–18004). Briefly, membranes were incubated at 30° C. for 2 hours in HEPES binding buffer (50 mM HEPES pH 7.6, 7 mM $MgCl_2$, 2 mM EDTA and 2 units/ml of bacitracin) containing radiolabelled peptide (0.05 to 0.15 nM) with or without 100 nM unlabeled somatostatin. Following dilution with cold binding buffer, samples were centrifuged at 40,000×g for 15 minutes and the radioactivity associated with the pellets was measured in an LKB Clini-Gamma Counter. Specific binding was calculated as the difference between the amount of radioactivity bound in the absence (Total binding) and in the presence (Nonspecific Binding) of 100 nM unlabeled somatostatin. Curve fitting and data analysis was carried out as described previously (P. J. Brown et al., 1990, *J Biol. Chem.,* 265:17995–18004).

For immunoprecipitation reactions, cell membranes were preincubated with a radiolabelled somatostatin analog in the presence and absence of 100 nM unlabelled SRIF, centrifuged and then solubilized for 1 hour at 4° C. in HEPES binding buffer containing 1 mg/ml DβM, 0.2 mg/ml CHS, 10 μg/ml soybean trypsin inhibitor, 50 μg/ml bacitracin and 10 μg/ml leupeptin (P. J. Brown and A. Schonbrunn, 1993, *J. Biol. Chem.,* 268, 6668–6676). The detergent to protein ratio was usually 4: 1. After centrifugation at 100,000×g, the solubilized ligand-receptor complex was either quantitated by PEG precipitation or subjected to immunoprecipitation.

To measure the amount of ligand-receptor complex in the soluble fraction, PEG precipitation was performed as previously described (P. J. Brown and A. Schonbrunn, 1993, *J. Biol. Chem.,* 268, 6668–6676). Solubilized receptor (40 μl) was diluted with 860 μl of HEPES binding buffer and 100 μl of 0.6% bovine γ-globulin. Following the addition of 1 ml of 40% PEG (w/v), the solution was mixed vigorously and incubated at 4° C. for 30 minutes. Samples were then centrifuged at 3300×g for 25 minutes and the radioactivity in the pellet was quantitated.

For immunoprecipitation, antiserum (R1-201 or R1-203) was added to the ligand-receptor complex solubilized from CHO-R1 cells, to the desired final concentration and incubated at 4° C. for 3 to 20 hours, as convenient. Protein-A-Sepharose-4B (20 μl of a 50% suspension) was then added and the incubation was continued for another hour at 4° C. Following centrifugation at 10,000×g for 2 minutes, the pellet was washed with cold HEPES binding buffer containing 0.25 mg/ml DβM, and then analyzed in a Gamma Counter.

Immunoprecipitation Efficiency of sst1 receptor Antisera:

Receptor immunoprecipitating efficiency was calculated as the radioactivity precipitated by the antisera divided by the radioactivity precipitated by PEG times 100%. The data, shown below in Table 3, demonstrate both antisera, R1-201 and R1-203 efficiently immunoprecipitated the sst receptor expressed in CHO-R1 cells, even at high dilutions.

TABLE 3

IMMUNOPRECIPITATION OF THE *sst1* RECEPTOR

| PRECIPITATING AGENT | Precipitated Complex (cpm) | % |
|---|---|---|
| PEG | 7105 ± 665 | 100 |
| Immune serum R1-201 (1:500) | 7392 ± 102 | 100 |
| Immune serum R1-203 (1:1000) | 6118 ± 448 | 86.1 |

Specificity of sst1 receptor peptide Antisera:

To determine if the anti-sst1 receptor peptide antisera specifically recognized the sst1 receptor, the binding was competed with antigenic peptide. Membranes derived from CHO-K1 cells stably transfected with the rat sst1 receptor (CHO-R1) were analyzed following the immunoprecipitation procedures described above. As shown in Table 4, 71.3% of the soluble [$^{125}I$-$Tyr^{11}$] SRIF-sst1 receptor complex was precipitated by the immune serum, whereas pre-immune serum precipitated only 0.6% of the receptor. The addition of 10 μM peptide antigen during the incubation with antiserum completely inhibited immunoprecipitation of the complex, whereas unrelated peptides had no effect (data not shown). In a total of nine independent experiments, 67.3±2.3% (mean±SEM) of the soluble sst1 receptor-ligand complex was precipitated by the antibody (R1-201). This peptide antibody efficiently, and specifically immunoprecipitated the sst1 receptor.

TABLE 4

IMMUNOPRECIPITATION OF *sst1 RECEPTOR*

| Precipitating Agent | Precipitated Complex (cpm) | % |
|---|---|---|
| PEG | 8347 ± 225 | 100 |
| Pre-immune serum (R1-201) | 52 ± 8 | 0.6 |
| Immune serum (R1-201) | 5952 ± 270 | 71.3 |
| Immune serum (R1-201) + peptide antigen (10 μm) | 72 ± 37 | 0.9 |

Receptor Subtype Specificity of Anti-sstr1 Antisera:

To assay the receptor subtype specificity of the sst1 peptide antibody, the ability of the antiserum (R1-201) to precipitate different somatostatin receptors from transfected CHO-K1 cell lines was examined. As shown in Table 5, 56% of the [$^{125}I$-$Tyr^{11}$]SRIF-sst1 receptor complex was precipitated by the anti-sst1 receptor antibody (R1-201). In contrast, less than 1% of the sst2 or sst4 receptor complexes were precipitated. Similarly, less than 1% of sst3 receptor was immunoprecipitated by this antiserum. Thus, the sst1 peptide antibody is specific for sst receptor subtype 1, with no significant cross-reactivity with other subtypes.

TABLE 5

SPECIFICITY OF *sst1* RECEPTOR PEPTIDE ANTISERUM

| | Precipitated Complex | | |
|---|---|---|---|
| | PEG | Antiserum R1-201 | |
| Cell Line | (cpm) | cpm | % |
| CHO-R1 | 15075 ± 253 | 8395 ± 110 | 55.7 |
| CHO-R2 | 16212 ± 427 | 115 ± 19 | 0.7 |
| CHO-R4 | 12508 ± 349 | 46 ± 20 | 0.4 |

TABLE 5-continued

SPECIFICITY OF *sst1* RECEPTOR PEPTIDE ANTISERUM

| Cell Line | Precipitated Complex PEG (cpm) | Antiserum R1-201 cpm | % |
|---|---|---|---|
| CHO-R1 | 7105 ± 665 | 7392 ± 102 | 100 |
| CHO-R3 | 683 ± 140 | -0- | -0- |

Characteristics of the sst Receptor Precipitated by Anti-sst1 Receptor Antisera:

The nature of the receptor protein recognized by the sst1 receptor-specific antiserum was next characterized. To biochemically identify individual receptor subtypes, membranes were prepared from untransfected CHO-K1 cells, as well as from CHO-R1 and CHO-R2 cells. The membranes were affinity labeled with [$^{125}$I-Tyr$^{11}$, ANB-Lys$^{4}$]SRIF as described in Brown et al., 1990 *J. Biol. Chem.* 265:17995–18004). The binding reaction was carried out in the dark with [$^{125}$I-Tyr$^{11}$, ANB-Lys$^{4}$]SRIF as described above. Following centrifugation, membranes were resuspended in cold HEPES binding buffer to a final concentration of 0.1 mg/ml, and irradiated at 254 nm on ice for 10 minutes (Mineralight model R-52, Ultraviolet Products Inc., San Gabriel, Calif.) following the procedure described in Brown et al., 1990, *J. Biol. Chem.,* 265:17995–18004. The reaction was stopped by the addition of 1 M Tris-Cl, pH 7.6. Membranes were then pelleted, solubilized in sample buffer (62.5 mM Tris-Cl, pH 6.8, 2% SDS, 20% glycerol and 50 mM dithiothreitol) and analyzed by SDS polyacrylamide gel electrophoresis on 10% acrylamide gels according to the method of Laemmli (Laemmli, 1970, *Nature,* 227, 680–685). The gels were dried onto filter paper and exposed to Amersham Hyperfilm at −70° C., for 2 to 14 days. [$^{125}$I-Tyr$^{11}$, ANB-Lys$^{4}$]SRIF covalently labeled broad bands of 60 kDa and 85 kDa in CHO-R1 and CHO-R2 cells, respectively. Somatostatin (100 nM) inhibited photoaffinity labeling of these bands, as expected for high affinity receptors. However, the somatostatin analog SMS 201-995 (10 nM) only inhibited labeling in CHO-R2 membranes, consistent with the known high affinity of this analog for sst2 but not sst1 receptors (Bell et al. and Bruns et al. IN: CIBA Foundation Symposium Vol. 190 *Somatostatin and its Receptors,* 1995, John Wiley and Sons, pages 65–88 and 89–111). No specific labeling was observed in the parental CHO-K1 cell.

The molecular mass predicted for the rat sst1 and sst2 receptors from their DNA sequence is 43 Kda and 42 Kda, respectively. Both the higher apparent mass of the photoaffinity labelled proteins (60 and 85 Kda) and the diffuse migration patterns seen in the SDS polyacrylamide gels were consistent with multiple glycosylation sites on these two receptors. Thus, the proteins which were covalently labeled by [$^{125}$I-Tyr$^{11}$, ANB-Lys$^{4}$]SRIF displayed the biochemical and binding properties expected for these specific sst receptor subtypes.

To determine whether the 60 kDa protein from CHO-R1 cells could be specifically precipitated by the sst1 receptor-specific antibody, membranes which had been preincubated in the dark with [$^{125}$I-Tyr$^{11}$, ANB-Lys$^{4}$]SRIF in the presence or absence of 100 nM somatostatin were solubilized and then irradiated to covalently label the receptors. The photoaffinity labeled receptors were subjected to immunoprecipitation with the antiserum R1-201, and then analyzed by SDS polyacrylamide gel electrophoresis and autoradiography. No specifically labeled bands were observed in the immunoprecipitates from either CHO-K1 or CHO-R2 cells. However, a broad 60 kDa band was evident in the immunoprecipitate from Is CHO-R1 cells. Labeling of this band was prevented when the binding reaction was carried out in the presence of unlabeled somatostatin. Further, immunoprecipitation of this protein was competed by 10 $\mu$M antigen peptide. The peptide antibody R1-201 specifically precipitated the 60 kDa sst1 receptor protein.

Immunoprecipitation of G-proteins coupled to the sst1 receptor:

One diagnostic feature of G protein coupled receptors is that their binding affinity for agonists is reduced in the presence of GTP or non-hydrolyzable GTP analogs. (Birmbaumer et al., *Biochem. Biophys. Acta,* 1031:163–224, 1990) Further, addition of GTP to a preformed agonist-receptor-G protein complex causes rapid dissociation of the ligand by converting the receptors from a high affinity to a low affinity state.

The immunoprecipitated [$^{125}$I-Tyr$^{11}$]SRIF-receptor prepared from CHO-R1 cells as described above was resuspended in buffer either without or with 100 $\mu$M GTP$\gamma$S and incubated at 30° C. to allow some of the bound ligand to dissociate. In the absence of guanine nucleotide, 53% of the specifically bound [$^{125}$I-Tyr$^{11}$]SRIF dissociated from the precipitated receptor complex after a 10 minute incubation at 30° C. Addition of GTP$\gamma$S increased the rate of ligand dissociation so that 78% of the initially bound hormone was released. The ability of GTP$\gamma$S to stimulate ligand dissociation from the immunoprecipitated receptor complex demonstrated that functional G proteins remained bound to the receptor. These studies show that sst1 receptor immunoprecipitated by the subtype-specific anti-sst1 receptor antibody R1-201 is coupled to G proteins.

Cellular Expression of the sst1 Receptor:

Subtype-specific anti-somatostatin receptor antibodies are necessary to quickly and efficiently determine the specific subtypes present in a particular cell sample. The anti-sstr1 antibody R1-201 was used to determine if subtype-I receptors were present on sample cells. High affinity somatostatin receptors have been identified in both $GH_4C_1$ rat pituitary cells and AR4-2J rat pancreatic acinar cells. (Schonbrunn et al., *J. Biological Chemistry,* 253:6473–6783, 1978: Viguerie et al., *American Journal of Physiology,* 255:G113–G120, 1988), however, the receptor subtypes expressed in these cells have not been characterized. To determine whether these cells express the sst1 receptor protein, $GH_4C_1$ and AR4-2J cell membranes were incubated with [$^{125}$I-Tyr$^{11}$] SRIF, the ligand-receptor complex was solubilized and immunoprecipitated with the anti-sstr1 antibody following the procedure described above. As shown in Table 6, the R1-201 antiserum precipitated 44% of the total [$^{125}$I-Tyr$^{11}$] SRIF-sst receptor complex from $GH_4C_1$ cells but less than 1% of the complex from AR4-2J cells. (As shown in Example 2, infra, $GH_4C_1$ cells and AR4-2J cells both express sst2A receptor.) Hence, binding studies with the antiserum R1-201 indicated that functional sst1 receptor protein is expressed by $GH_4C_1$ cells but not by AR4-2J cells.

TABLE 6

CELL SPECIFIC EXPRESSION OF *sst1* RECEPTOR PROTEIN

| | Precipitated Complex | | |
|---|---|---|---|
| | | Antiserum R1-201 (cpm) | |
| Cell Line | PEG (cpm) | cpm | % |
| GH4C1 | 18312 ± 882 | 8121 ± 115 | 44.3% |
| Ar4-2J | 19188 ± 537 | 162 ± 60 | 0.8% |

Example 2

Identification of an antigenic peptide of sst2A receptor Two antigenic peptides corresponding to unique sequences of the mouse sst2A receptor were selected from the C-terminal end of the receptor and synthesized as described for Example 1.

| ANTIGEN | SEQUENCE | SEQ. ID NO. |
|---|---|---|
| Antigen 1 | CSGTEDGERSDSKQDK | 21 |
| Antigen 2 | CERSDSKQDKSRLNETTETQRT | 18 |
| mSSTR-2A | . . . VSGTEDGERSDSKQDKSRLNETTETQR T . . . | 5 |
| Theveniau antigen | SGTEDGERSDS | 22 |

Hydrophobicity analysis predicted Antigen 1 as the most useful peptide for antibody production. An antigen previously used by Theveniau et al., as described above, was contained in this region, however the Theveniau antigen was unable to effectively precipitate sstr2A from CHO-R2 cells or to detect sstr2A protein in immunoblots. Antigen-1 contained the Theveniau antigen plus additional sequences, as shown above.

Antigen-2 was selected to substantially overlap with the location of the sstr1-antigen selected for Example 1 which produced sstr1-specific antibodies. Both Antigen-1 and Antigen-2 were located in the putative intracellular portion of the receptor's C-terminus.

Production of anti-sst2A Receptor Antigen:

The peptide Antigens-i and 2 were coupled to keyhole limpet hemocyanin (KLH) through an amino terminal cysteine as described for Example 1. Rabbits were immunized with immunogen according to the protocol described for Example 1, and resulting antisera was assayed by ELISA and by immunoprecipitation capability as described for Example 1.

Two rabbits (R2-204 and R2-206) were immunized with Antigen-1 (which included the Theveniau Antigen) as described above, and another two rabbits (R2-87 and R2-88) were immunized with Antigen-2, which peptide is shifted downstream from Antigen-1 on the carboxy terminus. Immunization procedures, compositions, boosts, and bleeds followed the procedures described above for Example 1. Resulting immune sera were analyzed by ELISA to first determine the affinity of the antisera for the antigenic peptide. The titration data is shown in Table 7, and indicate a broad range of potencies for the different antisera. The titration analysis was used to adjust the amount of antisera used in subsequent studies so that the amount of antibody was approximately consistent across the sera tested.

TABLE 7

TITRATION OF *sstr2A* ANTISERA BY ELISA

| | A405 nm | | | |
|---|---|---|---|---|
| Antiserum | Antigen-2 | | Antigen-1 | |
| dilution | R2-87 | R2-88 | R2-204 | R2-206 |
| 1:250 | — | — | 3.21 | 3.20 |
| 1:500 | — | — | 3.19 | 3.66 |
| 1:1000 | 3.09 | 3.43 | 2.87 | 3.61 |
| 1:2000 | 2.89 | 3.47 | 2.17 | 3.14 |
| 1:4000 | 2.41 | 3.32 | 1.29 | 2.97 |
| 1:8000 | 2.03 | 3.22 | 1.21 | 2.19 |
| 1:16,000 | 1.36 | 2.76 | 0.67 | 2.00 |
| 1:32,000 | 0.86 | 2.19 | 0.41 | 1.01 |
| 1:64,000 | 0.59 | 1.63 | 0.35 | 0.75 |
| 1:128,000 | 0.44 | 1.07 | 0.27 | 0.59 |
| 1:256,000 | 0.38 | 0.73 | 0.24 | 0.40 |
| 1:512,000 | 0.35 | 0.50 | — | — |
| 1:1,024,000 | 0.32 | 0.38 | — | — |
| -0- | 0.31 | 0.29 | 0.31 | 0.32 |
| $ED_{50}$ | 1:10,000 | 1:50,000 | 1:3000 | 1:18,000 |

Binding Affinity of Anti-sstr2A Antisera for sstr2A peptides:

The apparent affinities of each antibody for its corresponding peptide antigen was determined by ELISA as described for Example 1, using an antibody dilution selected to have similar reactivity across the four antisera (approximately $2\times ED_{50}$). The data are shown in Table 8 and demonstrate that each antiserum bound its corresponding peptide antigen with a similar high affinity.

TABLE 8

BINDING OF ANTISERA TO *sstr2A* PEPTIDE

| Competing | Absorbance 405 nm | | | |
|---|---|---|---|---|
| *sstr2A* | Antigen-2 | | Antigen-1 | |
| Peptide Antigen (M) | R2-87 (1:5000) | R2-88 (1:25,000) | R2-204 (1:2000) | R2-206 (1:8000) |
| $1 \times 10^{-11}$ | 2.12 ± 0.21 | 1.02 ± 0.14 | 1.40 ± 0.07 | 2.17± 0.04 |
| $3 \times 10^{-11}$ | 2.28 ± 0.07 | 1.22 ± 0.12 | 1.40 ± 0.06 | 2.17 ± 0.05 |
| $1 \times 10^{-10}$ | 1.36 ± 0.02 | 0.56 ± 0.05 | 1.26 ± 0.03 | 2.00 ± 0.04 |
| $3 \times 10^{-10}$ | 1.92 ± 0.21 | 0.99 ± 0.14 | 1.06 ± 0.04 | 1.72 ± 0.05 |
| $1 \times 10^{-9}$ | 1.65 ± 0.14 | 0.81 ± 0.06 | 0.92 ± 0.03 | 1.27 ± 0.06 |
| $3 \times 10^{-9}$ | 1.37 ± 0.14 | 0.71 ± 0.07 | 0.73 ± 0.03 | 0.87 ± 0.05 |
| $1 \times 10^{-8}$ | 1.05 ± 0.11 | 0.55 ± 0.06 | 0.65 ± 0.03 | 0.73 ± 0.03 |
| $3 \times 10^{-8}$ | 0.67 ± 0.04 | 0.34 ± 0.04 | 0.39 ± 0.01 | 0.39 ± 0.03 |
| $1 \times 10^{-7}$ | 0.49 ± 0.05 | 0.25 ± 0.03 | 0.24 ± 0.03 | 0.17 ± 0.02 |
| $3 \times 10^{-7}$ | 0.26 ± 0.02 | 0.16 ± 0.03 | 0.09 ± 0.02 | 0.06 ± 0.02 |
| Calculated $ED_{50}$ (nM) | 5.1 ± 2.5 | 4.4 ± 2.9 | 2.7 ± 1.1 | 1.5 ± 0.3 |

Precipitation of the sst2A receptor by anti-sstr2A peptide antisera:

CHO-K1 cells stably transfected with the rat sst2A receptor (CHO-R2A) were used to determine if the anti-sstr2A peptide antisera produced above recognized the native sst2A receptor, following the immunoprecipitation procedures describe above for Example 1. As shown below in Table 9, antisera obtained from animals immunized with Antigen-2 effectively precipitated the sst2A receptor. In contrast, antisera obtained from animals immunized with Antigen-1 did not precipitate more than 1% of sstr2A. Similarly, the scientists who prepared and tested the Theveniau Antigen 2i4 were unable to induce antibodies which could immunoprecipitate sstr2 with high efficiency. (Theveniau et al., 1994, *J. Neurochem* 63:447–455.) These studies demonstrate the Antigen-2 sequence is useful in generating subtype-specific antibodies, but not Antigen-1 or its included 2i4 Theveniau antigen.

TABLE 9

IMMUNOPRECIPITATION OF THE SST2A RECEPTOR BY ANTI-SSTR2A PEPTIDE SERA

| Anti-serum | Anti-serum Dilution | [$^{125}$I-Tyr$^{11}$]SS-Receptor Complex Precipitated (cpm) |
|---|---|---|
| Antigen 1 | | |
| R2-204 | 1:100 | −61 ± 21 |
| R2-206 | 1:100 | 315 ± 99 |
| Antigen 2 | | |
| R2-87 | 1:100 | 2783 ± 291 |
| R2-88 | 1:1000 | 6161 ± 303 |

The efficiency of anti-sstr2A antiserum R2-88 to immunoprecipitate the sst2A receptor was evaluated in CHO-R2 cells according to the procedures described above for Example 1. The data are shown below in Table 10 and indicate a high efficiency in precipitating the sst2A receptor, even at low concentrations (high dilutions).

TABLE 10

EFFICIENCY OF R2-88 (ANTISERUM) IN IMMUNOPRECIPITATING *sstr2A*

| Precipitating Agent | | Precipitated Complex | |
|---|---|---|---|
| | Dilution | cpm | % |
| PEG | | 8493 ± 385 | 100% |
| R2-88 | 1:1000 | 6572 ± 0 | 77.4 |
| | 1:3333 | 5884 ± 72 | 69.3 |
| | 1:10,000 | 3720 ± 195 | 43.8 |
| | 1:33,333 | 1647 ± 110 | 19.3 |
| | 1:10,000 | 447 ± 21 | 5.3 |

Receptor Subtype-Specificity of Anti-sst2A Receptor Antisera:

The specificity of the anti-sstr2A antiserum R2-88 to immunoprecipitate the sst2A receptor was evaluated in CHO cells transfected with genes encoding receptors sstr1-4, respectively, using the methods described above for Example 1. As shown in Table 11, the anti-sst2A receptor antiserum R2-88 specifically precipitated receptor from CHO-R2 cells, expressing the sst2A receptor and not from cells expressing any other receptor subtype.

TABLE 11

SPECIFICITY OF SST2 RECEPTOR ANTISERUM

| | Precipitated Complex | | |
|---|---|---|---|
| | PEG | Antiserum R2-88 | |
| Cell Line | (cpm) | (cpm) | % |
| CHO-R1 | 7061 ± 120 | 264 ± 28 | 3.7 |
| CHO-R2 | 8842 ± 543 | 7277 ± 56 | 82.3 |
| CHO-R4 | 10010 ± 525 | 219 ± 36 | 2.2 |
| CHO-R2 | 6326 | 4331 ± 7 | 68.5 |
| CHO-R3 | 683 | 21 ± 11 | 3.1 |

Characterization of the sst receptor precipitated by anti-sst2 receptor antisera:

The nature of the receptor protein recognized by the sst2 receptor specific antiserum was next characterized. Membrane receptors were prepared from CHO-R1 and CHO-R2 cells and were solubilized and photoaffinity labelled with [$^{125}$I-Tyr$^{11}$, ANB-Lys$^{4}$]SRIF as described above. The photoaffinity labeled receptors were then immunoprecipitated with the sst2 receptor antibody R2-88 and the immunoprecipitates were analyzed by SDS polyacrylamide gel electrophoresis and autoradiography as described in Example 1. No specifically labeled bands were observed in the immunoprecipitate from CHO-R1 cells. However, a broad 80–90 kDa band was evident in the immunoprecipitate from CHO-R2 cells. Labeling of this band was prevented when the binding reaction was carried out in the presence of 100 nM unlabeled somatostatin. Further, immunoprecipitation of this protein was competed by 5 $\mu$M antigen peptide. Therefore the peptide antibody R2-88 specifically precipitated the 80–90 kDa sst2 receptor protein.

Identification of sst2 receptor-containing cells:

The anti-sstr2A antiserum R2-88 was used to identify cells containing sst2A receptors, using the methods described above for Example 1. Cell membranes of cells known to contain somatostatin receptors were prepared and receptors were precipitated with R2-88 as described above. The data, shown in Table 12, demonstrated that the subtype 2A-specific anti-receptor antiserum R2-88 precipitated receptor from each cell tested, indicating the presence of the sst2A receptor in these cells.

TABLE 12

CELL SPECIFIC EXPRESSION OF SSTR2 RECEPTOR PROTEIN

| | Precipitated Complex (cpm) | | |
|---|---|---|---|
| | | Antiserum R2-88 | |
| Cell Line | PEG | cpm | % |
| GH4C1 | 11075 ± 393 | 5917 ± 30 | 53.4 |
| Ar4-2J | 16145 ± 695 | 13980 ± 304 | 86.6 |
| AtT-20 | 17975 ± 255 | 7424 ± 211 | 41.3 |
| RINm5f | 3264 ± 472 | 1574 ± 84 | 48.2 |

The nature of the sst2A receptor protein in each of these cells was next characterized by SDS polyacrylamide gel analysis of the photoaffinity labelled receptors immunoprecipitated by the R2-88 antibody. Membrane receptors were prepared from each cell line shown in Table 12, solubilized and photoaffinity labelled with [$^{125}$I-Tyr$^{11}$, ANB-Lys$^{4}$]SRIF as described above. The photoaffinity labeled receptors were then immunoprecipitated with the sst2 receptor antibody R2-88 and the immunoprecipitates were analyzed by SDS polyacrylamide gel electrophoresis and autoradiography as described in Example 1. A broad band of 80–100 kDa, 90–100 kDa, or 80–95 kDa was specifically labelled and imnunoprecipitated from AR4-2J, AtT-20, and $GH_4C_1$ cells, respectively. In each case, immunoprecipitation was prevented by the antigen peptide, demonstrating antibody specificity. The slight differences in the molecular weights of the immunoprecipitated receptors probably results from cell specific glycosylation patterns. In conclusion, the peptide antibody R2-88 specifically precipitated the sst2A receptor protein from each of these lines.

Immunoprecipitation of G-proteins coupled to the sst2 receptor

The immunoprecipitated [$^{125}$-Tyr$^{11}$]SRIF-sst2A receptor complex prepared from $GH_4C$, cells as described above for Table 12, was resuspended in buffer either without or with 100 $\mu$M GTPγS and incubated at 25° C. to allow some of the bound ligand to dissociate as described in Example 1. In the absence of guanine nucleotide 12% of the specifically bound [$^{125}$I-Tyr$^{11}$]SRIF dissociated from the precipitated receptor complex after a 5 min incubation at 25° C. Addition of GTPγS markedly increased the rate of ligand dissociation so that 64% of the initially bound hormone was released in this time. The ability of GTPγS to stimulate ligand dissociation from the immunoprecipitated receptor complex demonstrates that functional G proteins remained bound to the receptor. Therefore, these studies show that the sst2 receptor immunoprecipitated by the subtype-specific anti-sst2A receptor antibody R2-88 is coupled to G proteins.

Example 3

Identification of an antigenic peptide of the sst4 receptor:

The carboxy terminal region of the sst4 receptor subtype was examined to identify a preferred antigenic peptide in the same general location as the antigenic peptides identified above in Examples 1 and 2 for sst1 and sst2A receptors. The following peptide was identified:

CQQEPMQAEPASKRVPFTKT. (Seq. ID No. 19)

This antigen was synthesized and prepared as an immunogen as described above for Examples 1 and 2.

Preparation and Analysis of Anti-sst4 receptor peptide antisera:

Antibodies against the selected antigen were raised in rabbits as described for Examples 1 and 2. Antisera produced was analyzed for binding to the sst4 receptor peptide antigen, and for ability to immunoprecipitate the sst4 receptor from transfected CHO cells as described above. As shown in Table 13, anti-sstr4 antiserum (R4-91) at a dilution of 1:25,000 bound the sstr4 antigenic peptide with high affinity ($ED_{50}$≈3 nM).

TABLE 13

BINDING OF ANTISERUM R4-91 TO *SSTR4* PEPTIDE

| Competing *sstr4* antigen peptide (M) | Absorbance 405 nm |
|---|---|
| 0 | 2.2705 |
| $1 \times 10^{-10}$ | 2.455 |
| $3 \times 10^{-10}$ | 2.015 |
| $1 \times 10^{-9}$ | 1.183 |
| $1 \times 10^{-8}$ | 1.185 |
| $1 \times 10^{-7}$ | 0.385 |
| $1 \times 10^{-6}$ | 0.075 |
| 0 (preImmune) | 0.037 |

The anti-sstr4 antisera also efficiently and selectively immunoprecipitated sstr4 from CHO-R4 cell membranes (see Table 14), but did not precipitate somatostatin receptors produced in CHO-R1 or CHO-R2 cells (see Table 15). Thus, the identified peptide antigen induced a specific anti-sst4 receptor antibody. Both rabbits injected with the R4 peptide (R4-91 and R4-92) produced high affinity antibodies capable of immunoprecipitating the sst4 receptor (Table 14).

TABLE 14

IMMUNOPRECIPITATION OF SSTR4

| Precipitating Agent | Precipitated Complex cpm | % |
|---|---|---|
| PEG | 4976 ± 76 | 100 |
| Immune serum R4-91 | 1799 | 37.5 |
| Immune serum R4-92 | 1270 | 26.5 |
| PEG | 10012 ± 506 | 100 |
| Pre-immune serum (R4-91) | 91 ± 8 | 0.9 |
| Immune serum (R4-91) | 4838 ± 239 | 48.3 |
| Immune serum (R4-91) + peptide antigen | 116 ± 12 | 1.2 |

TABLE 15

SPECIFICITY OF SSTR4 ANTISERUM

| | Precipitated Complex | | |
|---|---|---|---|
| | PEG | Antiserum R4-91 | |
| Cell Line | (cpm) | cpm | % |
| CHO-R1 | 706 ± 120 | 283 ± 18 | 4.0 |
| CHO-R2 | 8842 ± 544 | 197 ± 15 | 2.2 |
| CHO-R4 | 10010 ± 525 | 4838 ± 239 | 48.3 |

Characterization of the sst receptor precipitated by anti-sst4 receptor antiserum:

The nature of the receptor protein recognized the by sst4 receptor specific antiserum was next characterized. Membrane receptors were prepared from CHO-R4 cells, solubilized and photoaffinity labelled with [$^{125}$I-Tyr$^{11}$, ANB-Lys$^{4}$] SRIF as described above. The photoaffinity labeled receptors were then immunoprecipitated with the sst4 receptor antibody R4-91 and the immunoprecipitates were analyzed by SDS polyacrylamide gel electrophoresis and autoradiography as described in Example 1. A broad ≈60 kDa band was evident in the immunoprecipitate from CHO-R4 cells. Labeling of this band was prevented when the binding reaction was carried out in the presence of 100 nM unlabeled somatostatin. Further, immunoprecipitation of this protein was competed by 5 μM antigen peptide. Therefore the peptide antibody R4-91 specifically precipitated the sst4 receptor protein.

Example 4

Identification of an antigenic peptide of the sst5 receptor

The following antigenic peptide was selected in a region of the sst5 receptor overlapping the antigens identified above for the sst1, 2 and 4 receptors:

CDKSGRPQATLPTRSCEANGL. (Seq. ID No. 20)

This peptide is synthesized and prepared according to the methods described above for Examples 1, 2 and 3. Following the procedures described in Examples 1–3, the sstr5 peptide is injected into rabbits to induce antibodies which specifically bind and immunoprecipitate the sst5 receptor. Antisera screening and evaluation of the antibody's subtype specificity are performed as described above for Examples 1–3.

Example 5

Use of receptor-specific antibodies in Western Blots

An efficient method to screen for the presence of different somatostatin receptor proteins in tissues would utilize immunoblotting (Western blotting) procedures. Therefore, the ability of the receptor specific antisera produced as described in Examples 1–3 to detect corresponding somatostatin receptors was determined by this assay.

For immunoblot analysis, membranes were prepared from the parental CHO-K1 cells and CHO-K1 cells expressing either the sst1 or sst2 receptors (CHO-R1 or CHO-R2 cells) as described previously (Brown P J, *J Biol Chem.,* 265:17995–18004, 1990). Membrane proteins were dissolved in sample buffer (62.5 mM Tris.Cl, pH 6.8, 2% SDS, 20% glycerol, and 60 nM dithiothreitol) and electrophoresed on a 10% acrylamide SDS gel according to the method of Laemmli (Laemmli, U. K., *Nature* 227, 680–685, 1970). Proteins were electrophoretically transferred to PVDF membranes (0.2$\mu$, BioRad) by standard procedures (Harlow & Lane, Antibodies: A Laboratory manual (as referenced above) and the membranes were incubated for one hour at room temperature with either pre-immune serum or antiserum R1-201 or R2-88 diluted 1:1000 in 1% nonfat dry milk in TBS. Immunoreactive bands were detected by incubating the washed membranes for one hour with goat anti-rabbit IgG horseradish peroxidase (1:10,000, BioRad) and developing with the Amersham ECL kit according to the manufacturer's directions.

The R1-201 antibody reacted strongly with a broad band centered around 70 kDa in CHO-R1 cells. This reactivity was completely abolished by adding 1 $\mu$M peptide antigen during the antibody incubation. Further, this band was not detectable in either the parental CHO-K1 cells or in CHO-K1 cells expressing the sst2 receptor. Similarly, the R2-88 antipeptide antibody reacted strongly with a broad band of approximately 82 kDa in CHO-R2 cells. Again, reactivity was completely abolished by adding 1 $\mu$M peptide antigen during the antibody incubation, and this band was not detectable in either the parental CHO-K1 cells or in CHO-K1 cells expressing the sst1 receptor. Neither of the preimmune sera recognized the specific receptor band. Therefore both antipeptide antibodies tested specifically recognized their corresponding receptor proteins in immunoblots.

Example 6

Immunocytochemical detection of somatostatin receptor proteins with subtype specific antibodies Another efficient and sensitive method to screen for the presence of somatostatin receptor subtypes in tissues would utilize immunocytochemical staining. Therefore, the ability of the receptor specific antisera produced in Examples 1–3 to detect the corresponding somatostatin receptors was determined by this assay (P. Dournaud, Y. Z. Gu, A. Schonbrunn, J. Mazella, G. S. Tannenbaum and A. Beaudet, "Immunocytochemical Localization of the Somatostatin Receptor sstr2 in Rat Brain Using a Specific Anti-peptide Antibody, manuscript in preparation, 1995).

Untransfected COS cells and COS cells transfected with either the sst1 or sst2 receptors were incubated with R1-201 or R2-88 antiserum, and specific staining was determined by utilizing standard immunofluorescent staining protocols and analyzed by confocal microscopy. Cells transfected with the sst1 receptor were stained by R1-201 antiserum but not the R2-88 antiserum. Conversely, cells transfected with the sst2 receptor were stained by the R2-88 antiserum but not the R1-201 antiserum. Staining was inhibited by the corresponding antigen peptide (P. Dournaud et al, manuscript in preparation, 1995).

The distribution of somatostatin receptors in brain has been examined previously by radioligand autoradiography. However, this method does not distinguish between the receptor subtypes. Therefore, the somatostatin receptor antisera prepared in Examples 1–3 were evaluated for the ability to immunocytochemically localize specific receptor subtype proteins in frozen brain sections. Highly specific immunoreactivity with the R2-88 antibody was observed in selected brain regions. For example, in the rat parietal cortex, discrete cell body labeling occurred in the supragranular layers and dense fiber labeling was observed in the deep layers (P. Dournaud et al, manuscript in preparation, 1995). This distribution strikingly conforms to that of somatostatin binding detected by autoradiography in this region of the brain. Examination of sst2 receptor labeling in the amygdaloid complex showed marked differences between cell body labeling in the central nucleus and fiber labeling in the basolateral nucleus. In all cases, labeling with the R2-88 antiserum was completely blocked by excess antigen peptide (P. Dournaud et al, manuscript in preparation, 1995).

Therefore, these studies demonstrate the utility of the somatostatin receptor antisera for the detection and localization of individual receptor subtypes in tissue sections.

Example 7

Screening tissues for sst receptor-subtype expression

To analyze a tissue sample for the presence of the specific somatostatin receptor subtype, the tissue is immunologically reacted with one or more of a panel of specific anti-somatostatin receptor subtype antibodies. These antibodies may include those produced by the examples described above; antibodies produced in alternative species to peptide antigens substantially corresponding to the peptide antigens described above, while perhaps differing slightly in amino acid composition; and also peptide antigens comprising functional derivatives of those peptide antigens described above.

The tissue may be screened, for example by preparing membranes from the tissue and immunoprecipitating somatostatin receptor with the specific anti-somatostatin receptor subtype antibodies according to the procedures described above. Alternatively, dot blot or western blot analysis on partially purified receptor proteins may be used. In yet another embodiment, tissue slices may be probed with one or more specific anti-somatostatin receptor subtype antibodies by immunochemical staining methods.

Example 8

Diagnostic Use

The ability to identify somatostatin receptor subtypes in tissue or tumor biopsies by immunological methods is likely to provide important information for the selection of therapy and disease classification. For example, many tissues and cancers have been shown to contain high density of receptors for somatostatin, including neuroendocrine tumors (e.g. growth hormone secreting pituitary adenomas and gastroenteropancreatic tumors such as carcinoids and islet cell carcinomas). Further, long-term therapy with the somatostatin analog octreotide can be used to control hormonal hypersecretion by such tumors, with resulting improvement in patient symptoms. Comparative studies measuring somatostatin receptors in vitro and octreotide effects on hormonal hypersecretion in vivo demonstrated that the somatostatin receptors expressed in these tumors represented the molecular basis for the octreotide action on hormone secretion (Reubi et al 1990, Cancer Res 50:5969–77). Therefore, the identification of particular somatostatin receptor subtypes in the diseased target tissue or tumor from individual patients will indicate the optimal choice of therapeutic drug for interacting with the identified receptors, will allow patient selection for treatment with particular somatostatin receptor-directed drugs and will predict the efficacy of such drugs for therapy. Moreover, the presence or absence of particular receptor subtypes can provide information about the differentiation state of the tissue sample and hence prognostic information about the likely course of the disease. For example, the absence of somatostatin receptors in carcinoids is thought to indicate the presence of poorly differentiated tumors which often produce a more malignant disease outcome.

In an optimal embodiment, an immunocytochemical kit is provided for identifying all known somatostatin receptor subtypes in a tissue biopsy from a patient. Positive reactivity with one ore more of the antibodies will demonstrate the presence of particular somatostatin receptors in the biopsy. Based on the known reactivity of pharmacological compounds with individual somatostatin receptor subtypes, a disease diagnosis is made and an appropriate drug is selected for therapy.

In a different embodiment, a somatostatin receptor antibody could be used to differentiate between a mutant and wild type form of the receptor and therefore determine whether such a mutation was responsible for a diseased state.

Example 9

Receptor purification

Purified somatostatin receptor subtype proteins can be prepared by standard methods utilizing a specific somatostatin receptor antibody for affinity adsorption. Such methods generally involve identifying an appropriate source of receptor or receptor fragment containing the antigen epitope, solubilizing the preparation and passing the crude mixture over an antibody-containing affinity matrix. The specific receptor will be bound by the immobilized antibody, while unrelated proteins will not and can be washed away. The receptor is then eluted from the antibody by standard methods. The purified receptor preparation will have a number of uses, for example as immunogen for preparation of receptor antibodies binding to different regions of the receptor protein or for screening of compounds for receptor binding.

I claim:

1. A method for determining a somatostatin receptor subtype having a seven transmembrane domain structure expressed by a tissue, a tissue slice, a tissue section, a tumor, or a tumor biopsy, cell isolate, or cell extract, comprising the steps of selecting a particular somatostatin receptor subtype having a seven transmembrane domain structure;

identifying, within said particular somatostatin receptor subtype an identified amino acid sequence, said identified amino acid sequence comprising about 10–30 amino acids near the carboxy terminus and being positioned about 20 residues to about 70 residues downstream from the seventh putative transmembrane domain as it exits the membrane and projects intracellularly p1 selecting a given amino acid sequence within said identified amino acid sequence;

synthesizing a peptide antigen comprising said given amino acid sequence;

producing antibodies to said peptide antigen, screening said antibodies for anti-somatostatin receptor subtype specific antibodies which specifically recognize and distinguish said particular somatostatin receptor subtype, said screening comprising:

reacting said antibodies against said particular somatostatin receptor subtype, and separately reacting said antibodies against different somatostatin receptor subtypes:

selecting somatostatin receptor subtype-specific antibodies which specifically react with only said particular somatostatin receptor subtype and not with different somatostatin receptor subtypes or any other protein;

reacting said somatostatin receptor subtype-specific antibodies with said tissue, or said tissue slice, tissue section, tumor, or tumor biopsy, cell isolate, or cell extract; and correlating reactivity of said somatostatin receptor subtype-specific antibodies to the presence of said particular somatostatin receptor subtype.

2. The method of claim 1, wherein said identified amino acid sequence begins approximately 10 residues after the first intracellular cysteine after the seventh putative transmembrane domain of said somatostatin receptor subtype.

3. The method of claim 1, wherein said identified amino acid sequence begins approximately 10 residues after the putative palmitoylation site cysteine of said somatostatin receptor subtype.

4. The method of claim 1, wherein said identified amino acid sequence begins approximately 20–30 amino acid residues downstream from the seventh putative transmembrane domain of said somatostatin receptor subtype.

5. The method of claim 1, wherein said given amino acid sequence is selected from the group consisting of SEQ ID NO: 17, 18, 19, 20, 36, 37, 38, 39 and 40.

6. The method of claim 1 , wherein synthesizing said peptide antigen is accomplished via solid-phase chemical synthesis.

7. The method of claim 1 , wherein synthesizing said peptide antigen is accomplished via recombinant technology.

8. The method of claim 1, wherein producing antibodies to said peptide antigen comprises the steps of:

administering said peptide antigen to a host animal to induce antibody production against said peptide antigen in said host animal;

monitoring antibody titer produced by said administration of said antigen to said host animal;

isolating antisera produced in said host animal by said administration of said peptide antigen; and selecting antisera, from said isolated antisera produced in said host, that is capable
of binding to said peptide antigen.

9. The method of claim 1, wherein said subtype-specific anti-somatostatin receptor antibody is a subtype 1-specific anti-somatostatin receptor antibody.

10. The method of claim 8, wherein the amino acid sequence of said peptide antigen is selected from the group consisting of SEQ ID NO: 17 and SEQ ID NO: 36.

11. The method of claim 1, wherein said subtype-specific anti-somatostatin receptor antibody is a subtype 2A-specific antibody.

12. The method of claim 11, wherein the amino acid sequence of said peptide antigen is selected from the group consisting of SEQ ID NO: 18 and SEQ ID NO: 37.

13. The method of claim 1, wherein said subtype-specific anti-somatostatin receptor antibody is a subtype 4-specific antibody.

14. The method of claim 13, wherein the amino acid sequence of said peptide antigen is selected from the group consisting of SEQ ID NO: 19, and SEQ ID NO: 38.

15. The method of claim 1, wherein said subtype-specific anti-somatostatin receptor antibody is a subtype 5-specific antibody.

16. The method of claim 15, wherein the amino acid sequence of said peptide antigen is selected from the group consisting of SEQ ID NO: 20, 39, and 40.

17. The method of claim 1, wherein said peptide antigen is chemically coupled to a carrier protein in order to increase antigenicity of said peptide antigen.

18. The method of claim 1, wherein said peptide antigen is synthesized by recombinant technology as a fusion protein in order to increase antigenicity of said peptide antigen.

19. The method of claim 8, wherein said administration of said peptide antigen further comprises the administration of an adjuvant to increase said host antibody production in response to said peptide antigen administration.

20. The method of claim 8, wherein said administering of said peptide antigen is selected from the group consisting of intradermal, subcutaneous, and intramuscular injection.

21. The method of claim 8, wherein said monitoring of said antibody titer production is by monthly bleeds of said host.

22. The method of claim 1, wherein said screening of said synthesized peptide for the ability to induce subtype-specific anti-somatostatin receptor antibodies comprises the steps of:

isolating antiserum produced from a host animal after said host animal has been injected with said peptide antigen;

measuring the binding of said antiserum to said peptide antigen; identifying antisera capable of binding to said peptide antigen;

measuring the binding of said antiserum capable of binding to said peptide antigen to said somatostatin receptor subtype;

identifying antiserum capable of binding to said peptide antigen that is also capable of binding to said somatostatin receptor subtype; and selecting said peptide antigen capable of producing said identified antiserum capable of binding to both said peptide antigen and said somatostatin receptor subtype.

23. The method of claim 22, wherein said measuring of said binding of said antiserum to said peptide antigen is via an enzyme-linked immunosorbent assay.

24. The method of claim 22, wherein said measuring of said binding of said antiserum to said somatostatin receptor is via immunoprecipitation comprising the steps of:

preincubating somatostatin receptor-containing plasma membranes with a radiolabeled ligand somatostatin analog;

forming somatostatin receptor-radiolabeled ligand somatostatin analog complexes:

solubilizing said somatostatin receptor-radiolabeled somatostatin ligand complexes;

precipitating said receptors of said complex with said identified antisera capable of binding to said peptide antigen;

quantitating the amount of said precipitated ligand-receptor complex using said identified antisera capable of binding to said peptide antigen; and selecting said antisera capable of binding to both said peptide antigen and said somatostatin receptor subtype.

25. A method for producing a somatostatin receptor subtype-specific antibody that specifically recognizes and distinguishes a specific somatostatin receptor subtype having a seven transmembrane domain structure, comprising the steps of:

selecting a particular somatostatin receptor subtype having a seven transmembrane domain structure;

identifying, within said particular somatostatin receptor subtype, an identified amino acid sequence, said identified amino acid sequence comprising about 10–30 amino acids near the carboxy terminus and being positioned about 20 residues to about 70 residues downstream from the seventh putative transmembrane domain as it exits the membrane and projects intracellularly;

selecting a given amino acid sequence within said identified amino acid sequence;

synthesizing a peptide antigen comprising said given amino acid sequence;

producing antibodies to said peptide antigen;

screening said antibodies for anti-somatostatin receptor subtype specific antibodies which specifically recognize and distinguish said particular somatostatin receptor subtype, said screening comprising:

reacting said antibodies against said particular somatostatin receptor subtype, and separately reacting said antibodies against different somatostatin receptor subtypes; and selecting subtype-specific antibodies which specifically react with only said particular somatostatin receptor subtype and not with different somatostatin receptor subtypes or any other protein.

26. The method of claim 25, wherein said identified amino acid sequence comprises about 15–25 amino acids.

27. The method of claim 25, wherein said identified amino acid sequence begins approximately 10 residues after the first intracellular cysteine after the seventh putative transmembrane domain of said somatostatin receptor subtype.

28. The method of claim 25, wherein said identified amino acid sequence begins approximately 10 residues after the putative palmitoylation site cysteine of said somatostatin receptor subtype.

29. The method of claim 25, wherein said identified amino acid sequence begins approximately 20–30 amino acid residues downstream from the seventh putative transmembrane domain of said somatostatin receptor subtype.

30. The method of claim 25, wherein said given amino acid sequence is selected from the group consisting of SEQ ID NO: 17, 18, 19, 20, 36, 37, 38, 39 and40.

* * * * *